United States Patent
Rosenthal et al.

(10) Patent No.: US 11,207,337 B2
(45) Date of Patent: Dec. 28, 2021

(54) CO-THERAPY COMPRISING CANAGLIFLOZIN AND PHENTERMINE FOR THE TREATMENT OF OBESITY AND OBESITY RELATED DISORDERS

(71) Applicant: Janssen Pharmaceutica NV, Beerse (BE)

(72) Inventors: Norman R. Rosenthal, Hopewell, NJ (US); Paul Rothenberg, Raritan, NJ (US); David C. Polidori, Rancho Sante Fe, CA (US); Douglas K. Ways, Ringoes, NJ (US); Peter P. Stein, Princeton Junction, NJ (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 16/820,767

(22) Filed: Mar. 17, 2020

(65) Prior Publication Data
US 2020/0215090 A1    Jul. 9, 2020

Related U.S. Application Data

(63) Continuation of application No. 16/245,682, filed on Jan. 11, 2019, which is a continuation of application No. 15/262,038, filed on Sep. 12, 2016, now abandoned.

(60) Provisional application No. 62/306,110, filed on Mar. 10, 2016, provisional application No. 62/218,842, filed on Sep. 15, 2015.

(51) Int. Cl.
*A61K 31/7042* (2006.01)
*A61K 31/135* (2006.01)
*A61K 31/137* (2006.01)

(52) U.S. Cl.
CPC ........ *A61K 31/7042* (2013.01); *A61K 31/135* (2013.01); *A61K 31/137* (2013.01)

(58) Field of Classification Search
None
See application file for complete search history.

(56) References Cited

U.S. PATENT DOCUMENTS

| | | |
|---|---|---|
| 2,799,241 A | 7/1949 | Wurster |
| 4,160,861 A | 7/1979 | Cole et al. |
| 4,584,369 A | 4/1986 | Klein et al. |
| 5,149,838 A | 9/1992 | Humphrey et al. |
| 5,292,461 A | 3/1994 | Juch et al. |
| 5,401,435 A | 3/1995 | Burzio et al. |
| 5,424,406 A | 6/1995 | Tsujihara et al. |
| 5,610,294 A | 3/1997 | Lam et al. |
| 5,731,292 A | 3/1998 | Tsujihara et al. |
| 5,767,094 A | 6/1998 | Tsujihara et al. |
| 5,780,483 A | 7/1998 | Widdowson et al. |
| 5,830,873 A | 11/1998 | Tsujihara et al. |
| 5,861,385 A | 1/1999 | Angerbauer et al. |
| 5,945,533 A | 8/1999 | Kometani et al. |
| 6,048,842 A | 4/2000 | Tsujihara et al. |
| 6,069,238 A | 5/2000 | Hitchcock et al. |
| 6,153,632 A | 11/2000 | Rieveley |
| 6,277,833 B1 | 8/2001 | Angerbauer et al. |
| 6,297,363 B1 | 10/2001 | Kubo et al. |
| 6,414,126 B1 | 7/2002 | Ellsworth et al. |
| 6,420,513 B2 | 7/2002 | Minami |
| 6,448,415 B1 | 9/2002 | Lee et al. |
| 6,475,521 B1 | 11/2002 | Timmins et al. |
| 6,515,117 B2 | 2/2003 | Ellsworth et al. |
| 6,562,791 B1 | 5/2003 | Maurya et al. |
| 6,617,313 B1 | 9/2003 | Maurya et al. |
| 6,627,611 B2 | 9/2003 | Tomiyama et al. |
| 6,800,761 B1 | 10/2004 | Franc et al. |
| 7,008,959 B2 | 3/2006 | Franc et al. |

(Continued)

FOREIGN PATENT DOCUMENTS

| | | |
|---|---|---|
| CA | 2494177 A1 | 2/2004 |
| EP | 0355750 A1 | 2/1990 |

(Continued)

OTHER PUBLICATIONS

Adachi et al., "T-1095, a Renal Na+-Glucose Transporter Inhibitor, Improves Hyperglycemia in Streptozotocin-Induced Diabetic Rats.", *Metabolism*, Aug. 2000, pp. 990-995, vol. 49(8).

Aghamohannadzadeh, et al., *Therapeutic Advances in Endocrinology and Metabolism*, 2015, pp. 56-60, vol. 6(2).

Ahmad et al., "Synthesis and Structure Determination of Some Oxadiazole-2-Thione and Triazole-3-Thione Galactosides.", *Nucleosides, Nucleotides & Nucleic Acids*, 2001, pp. 1671-1682, vol. 20(9).

Albertoni Borghese et al., "Inhibitors of sodium/glucose cotransport.", *Drugs of the Future*, Apr. 2009, pp. 297-305, vol. 34(4), Prous Science, XP007915342.

(Continued)

*Primary Examiner* — Dale R Miller

(57) ABSTRACT

The present invention is directed to the use of co-therapy comprising administration of canagliflozin and phentermine for the treatment of obesity and obesity related disorders. More particularly, the present invention is directed to co-therapy for treating obesity, for promoting weight loss and/or for suppressing appetite; for treating, delaying, slowing the progression of and/or preventing metabolic disorders (including for example Type 2 diabetes mellitus); for treating, delaying, slowing the progression of and/or preventing renal or fatty liver disorders (including for example NASH, NAFLD, etc.); for treating, delaying, slowing the progression of and/or preventing sleep disorders (including for example sleep apnea); for providing cardiovascular protection; for treating, delaying, slowing the progression of and/or preventing cardiovascular events (including major adverse cardiac events (MACE) such as myocardial infarction, unstable angina, cardiovascular death, revascularization, fatal or non-fatal cerebrovascular accident, peripheral arteriopathy, aortic events, hospitalization due to congestive heart failure, etc.); and/or for extending or prolonging life span.

10 Claims, 1 Drawing Sheet

(56) References Cited

U.S. PATENT DOCUMENTS

| | | |
|---|---|---|
| 7,045,665 B2 | 5/2006 | Fujikura et al. |
| 7,074,826 B2 | 7/2006 | Wechter et al. |
| 7,084,123 B2 | 8/2006 | Fujikura et al. |
| 7,157,584 B2 | 1/2007 | Kuroita et al. |
| 7,202,350 B2 | 4/2007 | Imamura et al. |
| 7,271,153 B2 | 9/2007 | Nishimura et al. |
| 7,288,528 B2 | 10/2007 | Frick et al. |
| 7,294,618 B2 | 11/2007 | Fushimi et al. |
| 7,375,213 B2 | 5/2008 | Deshpande et al. |
| 7,417,032 B2 | 8/2008 | Eckhardt et al. |
| 7,511,022 B2 | 3/2009 | Beavers et al. |
| 7,566,699 B2 | 7/2009 | Fushimi et al. |
| 7,576,064 B2 | 8/2009 | Kikuchi et al. |
| 7,666,845 B2 | 2/2010 | Cook et al. |
| 7,932,379 B2 | 4/2011 | Deshpande et al. |
| 7,943,582 B2 | 5/2011 | Nomura et al. |
| 7,943,788 B2 | 5/2011 | Nomura et al. |
| 2001/0041674 A1 | 11/2001 | Tomiyama et al. |
| 2002/0032164 A1 | 3/2002 | Dale et al. |
| 2002/0052326 A1 | 5/2002 | Washburn |
| 2002/0111315 A1 | 8/2002 | Washburn et al. |
| 2003/0024914 A1 | 2/2003 | Aleshin |
| 2003/0064935 A1 | 4/2003 | Gougoutas |
| 2003/0087843 A1 | 5/2003 | Washburn |
| 2003/0114390 A1 | 6/2003 | Washburn et al. |
| 2003/0191121 A1 | 10/2003 | Miller et al. |
| 2004/0053855 A1 | 3/2004 | Fujikura et al. |
| 2004/0063646 A1 | 4/2004 | Fujikura et al. |
| 2004/0110936 A1 | 6/2004 | Ohsumi et al. |
| 2004/0116357 A1 | 6/2004 | Fushimi et al. |
| 2004/0132669 A1 | 7/2004 | Nishimura et al. |
| 2004/0138143 A1 | 7/2004 | Glombik et al. |
| 2004/0259819 A1 | 12/2004 | Frick et al. |
| 2005/0014704 A1 | 1/2005 | Frick et al. |
| 2005/0032711 A1 | 2/2005 | Patel et al. |
| 2005/0032712 A1 | 2/2005 | Urbanski |
| 2005/0037980 A1 | 2/2005 | Rybczynski et al. |
| 2005/0037981 A1 | 2/2005 | Beavers et al. |
| 2005/0049203 A1 | 3/2005 | Nishimura et al. |
| 2005/0124555 A1 | 6/2005 | Tomiyama et al. |
| 2005/0124556 A1 | 6/2005 | Burton |
| 2005/0209166 A1 | 9/2005 | Eckhardt et al. |
| 2005/0233988 A1 | 10/2005 | Nomura et al. |
| 2005/0256317 A1 | 11/2005 | Sato et al. |
| 2006/0009400 A1 | 1/2006 | Eckhardt et al. |
| 2006/0035841 A1 | 2/2006 | Eckhardt et al. |
| 2006/0122126 A1 | 6/2006 | Imamura et al. |
| 2006/0189548 A1 | 8/2006 | Himmelsbach et al. |
| 2006/0217323 A1 | 9/2006 | Patel et al. |
| 2006/0229260 A1 | 10/2006 | Rybczynski et al. |
| 2006/0234954 A1 | 10/2006 | Urbanski |
| 2006/0247179 A1 | 11/2006 | Fushimi et al. |
| 2006/0258749 A1 | 11/2006 | Eckhardt et al. |
| 2006/0293251 A1 | 12/2006 | Urbanski et al. |
| 2007/0027092 A1 | 2/2007 | Himmelsbach et al. |
| 2007/0049537 A1 | 3/2007 | Eckhardt et al. |
| 2007/0060531 A1 | 3/2007 | Kikuchi et al. |
| 2007/0060545 A1 | 3/2007 | Nomura et al. |
| 2008/0027122 A1 | 1/2008 | Nomura et al. |
| 2008/0119422 A1 | 5/2008 | Nomura et al. |
| 2008/0132563 A1 | 6/2008 | Kakinuma et al. |
| 2008/0146515 A1 | 6/2008 | Nomura et al. |
| 2008/0234366 A1 | 9/2008 | Bindra et al. |
| 2009/0124702 A1 | 5/2009 | Siva Satya Krishna Babu et al. |
| 2009/0233874 A1 | 9/2009 | Abdel-Magid et al. |
| 2010/0099883 A1 | 4/2010 | Filliers et al. |
| 2011/0009347 A1 | 1/2011 | Liang et al. |
| 2011/0087017 A1 | 4/2011 | Farina et al. |
| 2011/0212905 A1 | 9/2011 | Nomura et al. |
| 2012/0058941 A1 | 3/2012 | Nomura et al. |
| 2012/0115799 A1 | 5/2012 | Wang et al. |

FOREIGN PATENT DOCUMENTS

| | | |
|---|---|---|
| EP | 0348184 B1 | 3/1993 |
| EP | 0579204 A2 | 1/1994 |
| EP | 0579204 A3 | 1/1994 |
| EP | 0625513 B1 | 9/1999 |
| EP | 1172362 A1 | 1/2002 |
| EP | 1338603 A1 | 8/2003 |
| EP | 1528066 A1 | 5/2005 |
| EP | 1845095 | 10/2007 |
| EP | 1956023 A1 | 3/2008 |
| GB | 2359554 | 8/2001 |
| JP | 59039889 A | 3/1984 |
| JP | 63-233975 A | 9/1988 |
| JP | 4-253974 A | 9/1992 |
| JP | 06256354 A | 9/1994 |
| JP | 07242526 A | 9/1995 |
| JP | 9-263549 A | 10/1997 |
| JP | 2000-34230 A | 2/2000 |
| JP | 2000-34239 A | 2/2000 |
| JP | 2001-288178 A | 10/2001 |
| JP | 2002167430 A | 6/2002 |
| JP | 2003-012686 A1 | 1/2003 |
| JP | 2003238417 A | 8/2003 |
| JP | 2003313168 A | 11/2003 |
| JP | 2011-522896 A | 8/2011 |
| WO | WO 1993/09100 A1 | 5/1993 |
| WO | WO 1993/21178 A1 | 10/1993 |
| WO | WO 1994/14807 A1 | 7/1994 |
| WO | WO 1997/17949 A1 | 5/1997 |
| WO | WO 1997/25033 A1 | 7/1997 |
| WO | WO 1998/42347 A1 | 10/1998 |
| WO | WO 1999/67236 A | 12/1999 |
| WO | WO 2000/27823 A1 | 5/2000 |
| WO | WO 2000/28989 A1 | 5/2000 |
| WO | WO 2000/74681 A1 | 12/2000 |
| WO | WO 2001/127128 | 4/2001 |
| WO | WO 2001/032157 A2 | 5/2001 |
| WO | WO 2001/64669 A1 | 9/2001 |
| WO | WO 2001/68660 A1 | 9/2001 |
| WO | WO 2001/74834 A1 | 10/2001 |
| WO | WO 2001/74835 A1 | 10/2001 |
| WO | WO 2001/085167 A1 | 11/2001 |
| WO | WO 2002/026706 A2 | 4/2002 |
| WO | WO 2002/053573 A1 | 7/2002 |
| WO | WO 2002/068439 A1 | 9/2002 |
| WO | WO 2002/068440 A1 | 9/2002 |
| WO | WO 2002/070020 A2 | 9/2002 |
| WO | WO 2002/070020 A3 | 9/2002 |
| WO | WO 2002/083066 A2 | 10/2002 |
| WO | WO 2002/088157 A1 | 11/2002 |
| WO | WO 2002/094262 A1 | 11/2002 |
| WO | WO 2002/096357 A2 | 12/2002 |
| WO | WO 2003/000712 A1 | 1/2003 |
| WO | WO 2003/011880 A1 | 2/2003 |
| WO | WO 2003/020737 A1 | 3/2003 |
| WO | WO 2003/043621 A1 | 5/2003 |
| WO | WO 2003/087104 A1 | 10/2003 |
| WO | WO 2003/099836 A1 | 12/2003 |
| WO | WO 2004/007517 A1 | 1/2004 |
| WO | WO 2004/013118 A1 | 2/2004 |
| WO | WO 2004/014931 A1 | 2/2004 |
| WO | WO 2004/019958 A1 | 3/2004 |
| WO | WO 2004/052902 A1 | 6/2004 |
| WO | WO 2004/052903 A1 | 6/2004 |
| WO | WO 2004/063209 A2 | 7/2004 |
| WO | WO 2004/063209 A3 | 7/2004 |
| WO | WO 2004/064806 A | 8/2004 |
| WO | WO 2004/076470 A2 | 9/2004 |
| WO | WO 2004/080990 A1 | 9/2004 |
| WO | WO 2004/087727 A1 | 10/2004 |
| WO | WO 2004/099230 A1 | 11/2004 |
| WO | WO 2004/113359 A1 | 12/2004 |
| WO | WO 2005/009539 A2 | 2/2005 |
| WO | WO 2005/009954 A2 | 2/2005 |
| WO | WO 2005/012326 A1 | 2/2005 |
| WO | WO 2005/058845 A2 | 6/2005 |
| WO | WO 2006/010557 | 2/2006 |
| WO | WO 2006/080577 A1 | 8/2006 |

(56) References Cited

FOREIGN PATENT DOCUMENTS

| WO | WO 2006/108842 A1 | 10/2006 |
|---|---|---|
| WO | WO 2007/025943 A2 | 3/2007 |
| WO | WO 2007/031548 A2 | 3/2007 |
| WO | WO 2007/087441 A2 | 8/2007 |
| WO | WO 2008/013322 A1 | 1/2008 |
| WO | WO 2008/020011 A1 | 2/2008 |
| WO | WO 2008/034859 A1 | 3/2008 |
| WO | WO 2008/055870 A1 | 5/2008 |
| WO | WO 2008/055940 A2 | 5/2008 |
| WO | WO 200/8069327 A1 | 6/2008 |
| WO | WO 2008/070609 A1 | 6/2008 |
| WO | WO 2009/022010 A1 | 2/2009 |
| WO | WO 2009/026537 | 2/2009 |
| WO | WO 2009/035969 A1 | 3/2009 |
| WO | WO 2009/091082 A1 | 7/2009 |
| WO | WO 2009/121945 A2 | 10/2009 |
| WO | WO 2009/152189 A1 | 12/2009 |
| WO | WO 2010/045656 A2 | 4/2010 |
| WO | WO 2010/092125 A1 | 8/2010 |
| WO | WO 2011/047113 A1 | 4/2011 |
| WO | WO 2011/142478 A1 | 11/2011 |

OTHER PUBLICATIONS

Amishiro et al., "Synthesis and Antitumor Activity of Duocarmycin Derivatives: A-Ring Pyrrole Compounds Bearing 5-Membered Heteroarylacryloyl Groups.", *Chem. Pharm. Bull.*, Oct. 1999, pp. 1393-1403, vol. 47(10).

Appleton et al., "A Mild and Selective C-3 Reductive Alkylation of Indoles.", *Tetrahedron Letters*, 1993, pp. 1529-1532, vol. 34(9).

Apsel et al., "General Entries to C-aryl glycosides. Formal synthesis of galtamycinone.", *Tetrahedron Letters*, 2003, pp. 1075-1077, vol. 44.

Arakawa et al., "Improved diabetic syndrome in C57BL/KsJ-db/db Mice by Oral Administration of the Na+-Glucose Cotransporter Inhibitor T-1095.", *British Journal of Pharmacology*, 2001, pp. 578-586, vol. 132.

Banker, *Modern Pharmaceutics*, Third Edition, Marcel Dekker, Inc., published 1996, p. 596.

Beck-Nielsen et al., "In Vivo Glucose Metabolism, Insulin Secretion and, Insulin Action in Europids with non-insulin-dependent Diabetes mellitus (NIDDM) and Their First-degree Relatives.", *Diabetic Medicine*, Sep. 1996, pp. S78-S84, vol. 13(9 Supp. 6).

Benhaddou et al.,"Tetra-n-propylammonium tetra-oxoruthenate(VII): a reagent of choice for the oxidation of diversely protected glycopyranoses and glycofuranoses to lactones.", *Carbohydrate Research*, 1994, pp. 243-250, vol. 260.

Bertolini et al., "A New Simple One-Pot Regioselective Preparation of Mixed Diesters of Carbonic Acid.", *Journal of Organic Chemistry*, 1998, pp. 6031-6034, vol. 63(17).

Blair et al., "Effect of Ring Fluorination on the Pharmacology of Hallucinogenic Tryptamines.", *J. Med. Chem.*, 2000, pp. 4701-4710, vol. 43.

Boehm et al., "Novel Inhibitors of DNA Gyrase: 3D Structure Based Biased Needle Screening, Hit Validation by Biophysical Methods, and 3D Guided Optimization. A Promising Alternative to Random Screening.", *J. Med. Chem.*, 2000, pp. 2664-2674, vol. 43(14).

Bookser, B.C., "2-Benzyloxymethy1-5-(tributylstannyptetrazole. A reagent for the preparation of 5-aryl-and 5-heteroaryl-1H-tetrazoles via the Stille reaction.", *Tetrahedron Letters*, 2000, pp. 2805-2809, vol. 41.

Bouillon et al., "Synthesis of novel halopyridinylboronic acids and esters. Part 2: 2,4, or 5-Halopyridin-3-yl-boronic acids and esters.", *Tetrahedron*, 2002, pp. 3323-3328, vol. 58.

Bouillon et al., "Synthesis of novel halopyridinylboronic acids and esters. Part 3: 2, or 3-Halopyridin-4-yl-boronic acids and esters.", *Tetrahedron*, 2002, pp. 4369-4373, vol. 58.

Bouillon et al., "Synthesis of novel halopyridinylboronic acids and esters. Part 4: Halopyridin-2-yl-boronic acids and esters are stable, crystalline partners for classical Suzuki cross-coupling.", *Tetrahedron*, 2003, pp. 10043-10049, vol. 59.

Braga et al., "Making crystals from crystals: a green route to crystal engineering and polymorphism.", *Chem. Commun.*, 2005, pp. 3635-3645.

Brooks et al., "Boron Trichloride/Tetra-n-Butylammonium Iodide: A Mild, Selective Combination Reagent for the Cleavage of Primary Alkyl Aryl Ethers.", *J. Org. Chem.*, 1999, pp. 9719-9721, vol. 64.

Brooks et al., "Dapagliflozin for the Treatment of Type 2 Diabetes.", *The Annals of Pharmacotherapy*, 2009, pp. 1286-1293, vol. 43.

CAS Reg. No. 487001-40-1, IP Organisers, Entered STN Feb. 7, 2003, pp. 1-2.

Caumo et al., "Insulin Sensitivity from Meal Tolerance Tests in Normal Subjects: A Minimal Model Index.", *J. of Clinical Endocrinology & Metabolism*, 2000, pp. 4396-4402, vol. 85(11).

Cicchillo et al., "A convenient synthesis of glycosyl chlorides from sugar hemiacetals using triphosgene as the chlorine source.", *Carbohydrate Research*, 2000, pp. 431-434, vol. 328.

Clayden et al., "Dearomatizing Cyclization of Arylsulfonylalkoxymethyl Lithiums: A Route to the Podophyllotoxin Skeleton.", *Organic Letters*, 2003, pp. 831-834, vol. 5(6).

Clinical Trial NTC00707954, ClinicalTrials.gov/archive/NTC00707954/2008_06_30, View of Trial on Jun. 30, 2008.

Comins et al., "Synthesis of 3-Substituted Indoles Via N-Acylindolium Ions.", *Tetrahedron Letters*, 1986, pp. 1869-1872, vol. 27(17).

Cottet et al., "Recommendable Routes to Trifluoromethyl-Substituted Pyridine—and Quinolinecarboxylic Acids.", *Eur. J. Org. Chem.*, 2003, pp. 1559-1568.

Czernecki et al., "C-Glycosides. 7. Stereospecific C-Glycosylation of Aromatic and Heterocyclic Rings.", *J. Org. Chem.*, 1989, pp. 610-612, vol. 54.

De Las Heras et al., "Alkylating Nucleosides 1. Synthesis and Cytostatic Activity of N-Glycosyl(halomethyl)-1,2,3-triazoles. A New Type of Alkylating Agent.", *Journal of Medicinal Chemistry*, 1979,pp. 496-501, vol. 22(5).

Deeg et al., "Pioglitazone and Rosiglitazone Have Different Effects on Serum Lipoprotein Particle Concentrations and Sizes in Patients With Type 2 Diabetes and Dyslipidemia.", *Diabetes Care*, Oct. 2007, pp. 2458-2464, vol. 30(10).

Deetjen et al., "Renal Handling of D-Glucose and Other Sugars.", *Textbook of Nephrology*, 3rd Edition, 1995, pp. 90-94. vol. 1.

Devivar et al., "Benzimidazole Ribonucleosides: Design, Synthesis, and Antiviral Activity of Certain 2-(Alkylthio)- and 2-(Benzylthio)-5,6-dichloro-1-(.beta.-D-ribofuranosyl)benzimidazolesl.", *J.Med. Chem.*, 1994, pp. 2942-2949, vol. 37.

Dewynter et al., "Synthesis of Pseudomucleosides containing Chiral Sulfahydantoins as Aglycone (II).", *Tetrahedron*, 1996, pp. 993-1004, vol. 52(3).

Dillard et al., "Indole Inhibitors of Human Nonpancreatic Secretory Phospholipase A2. 1. Indole-3-acetamides.", *J. Med. Chem.*, 1996, pp. 5119-5136, vol. 39.

Dinneen, S.F., "The Postprandial State: Mechanisms of Glucose Intolerance.", *Diabetic Medicine*, Aug. 1997, pp. S19-S24, vol. 14, Issue S3.

Dondoni et al., "Stereoselective synthesis of C-glycosylphosphonates from their ketols. Reconsideration of an abandoned route.", *Tetrahedron: Asymmetry*, 2000, pp. 305-317, vol. 11.

Dondoni et al., "Thiazole-Based Synthesis of Formyl C-Glycosides. ", *J. Org. Chem.* , 1994,. pp. 6404-6412, vol. 59.

Dudash et al., "Glycosylated dihydrochalcones as potent and selective sodium glucose co-transporter 2 (SGLT2) inhibitors.", *Bioorganic & Medicinal Chemistry Letters*, 2004, pp. 5121-2125, vol. 14.

Dunn et al., "Analgetic and antiinflammatory 7-Aroylbenzofuran-5-ylacetic acids and 7-Aroylbenzothiophene-5-ylacetic Acids.", *Journal of Med. Chem.*, 1986, pp. 2326-2329, vol. 29(1).

Eid et al., "Reaction of Some 1,2,4-Triazines with Acetobromoglucose. ", *Arch. Pharm.* (Weinheim), 1990, pp. 243-245, vol. 323.

Ellsworth et al., "Aglycone exploration of C-arylglucoside inhibitors of renal sodium-dependent glucose transporter SGLT2.", *Bioorganic & Medicinal Chemistry Letters*, 2008, pp. 4770-4773, vol. 18.

Ellsworth et al., "C-Arylglucoside synthesis: triisopropylsilane as a selective reagent for the reduction of an anomeric C-phenyl ketal.", *Tetrahedron: Asymmetry*, 2003, pp. 3243-3247, vol. 14.

Emancipator, K., "Laboratory diagnosis and monitoring of diabetes mellitus.", *Am J Clin Pathol.*, Nov. 1999, pp. 65-674, vol. 112(5).

(56) References Cited

OTHER PUBLICATIONS

Frahn et al., "Functionalized AB-Type Monomers for Suzuki Polycondensation.", *Synthesis*, Nov. 1997, pp. 1301-1304.
Fresneda et al., "Synthesis of the indole alkaloids meridianins from the tunicate Aplidium meridianum.", *Tetrahedron*, 2001, pp. 2355-2363, vol. 57.
Fuller et al., "Thienothiophenes. Part 2. Synthesis, metallation and bromine-lithium exchange reactions of thieno[3,2-b-thiophene and its polybromo derivatives.", *J. Chem. Soc.*, Perkin Trans. 1., 1997, pp. 3465-3470.
Ganesh et al., "Synthesis and biological evaluation of fluorescently labeled epothilone analogs for tubulin binding studies.", *Tetrahedron*, 2003, pp. 9979-9984, vol. 59.
Gershell, L., "Type 2 diabetes market.", *Nature Reviews Drug Discovery*, May 2005, pp. 367-368, vol. 4.
Gohier et al., "ortho-Metalation of Unprotected 3-Bromo and 3-Chlorobenzoic Acids with Hindered Lithium Dialkylamides.", *J. Org. Chem.*, 2003, pp. 2030-2033, vol. 68.
Goldberg R.B., "Prevention of Type 2 Diabetes.", *Medical Clinics of North America*, Jul. 1998, pp. 805-821, vol. 82(4).
Gong, H., et al., "Diasteroselective Ni-Catalyzed negishi Cross Coupling Approach to Saturated, Fully Oxygenated C-Alkyl and C-Aryl Glycosides.", *Journal of the American Chemical Society*, Sep. 10, 2008, pp. 12177-12183, vol. 130(36), XP002612364.
Goodman & Gilman's the Pharmacological Basis of Therapeutics, 10th Edition, McGraw-Hill Medical Publishing Division, 2001, pp. 54-57.
Greene et al., "Protective Groups in Organic Synthesis.", 3rd Edition, 1999, pp. 116-121.
Greene et al., "Protective Groups in Organic Synthesis.", 3rd Edition, 1999, pp. 170.
Gronowitz et al., "Some Substitution Reactions of 1-(2-Thienyl)pyrazole and 1-(3'-Thienyl)pyrazole.", *Chemica Scripta.*, 1979, pp. 157-161, vol. 13.
Groop et al., "Characterization of the Prediabetic State.", *American Journal of Hypertension*, Sep. 1997, pp. 172S-180S, vol. 10(9Part2).
Gros et al., "Efficient and Regioselective Access to Bis-heterocycles via Palladium-Catalysed Coupling of Organostannanes and Organozincates Derived from C-6 Lithiated 2-Methoxypyridine.", *Synthesis*, 1999, pp. 754-756, No. 5.
Haffner S.M., "Impaired Glucose Tolerance, Insulin Resistance and Cardiovascular Disease.", *Diabetic Medicine*, Aug. 1997, pp. S12-S18, vol. 14.
Haffner S.M., "The Prediabetic Problem: Development of Non-Insulin-Dependent Diabetes Mellitus and Related Abnormalities.", *Journal of Diabetes and Its Complications*, Mar.-Apr. 1997, pp. 69-76, vol. 11(2).
Han et al., "Dapagliflozin, a Selective SGLT2 Inhibitor, Improves Glucose Homeostasis in Normal and Diabetic Rats.", *Diabetes*, Jun. 2008, pp. 1723-1729, vol. 57, New York.
Handlon, A. L., "Sodium glucose co-transporter 2 (SGLT2) inhibitors as potential antidiabetic agents.", *Expert Opin. Ther. Patents*, 2005, pp. 1531-1540, vol. 15(11).
Hixon et al., "Sizing Materials by Crushing and Grinding.", *Chemical Engineer*, Nov. 1990, pp. 94-103.
Hofslokken et al., "Convenient Method for the ortho-Formylation of Phenols.", *Acta Chemica Scandinavica*, 1999, pp. 258-262, vol. 53.
Hongu et al., "Na+-Glucose Cotransporter Inhibitors as Antidiabetic Agents. II.1) Synthesis and Structure—Activity Relationships of 4'-Dehydroxyphlorizin Derivatives.", *Chem. Pharm. Bull.*, 1998, pp. 22-33, vol. 46(1).
Horton et al., "Synthetic Routes to Higher-Carbon Sugars. Reaction of Lactones with 2-Lithio-1,3-Dithiane.", *Carbohydrate Research*, 1981, pp. 27-41, vol. 94.
Hu et al., "A New Approach Towards the Yellowing Inhibition of Mechanical Pulps. Part I: Selective Removal of alpha-Hydroxyl and alpha-Carbonyl Groups in Lignin Model Compounds.", *Holzforschung*, 1999, pp. 43-48, vol. 53(1).

Huang-Minlon, "Reduction of Steroid Ketones and other Carbonyl Compounds by Modified Wolff-Kishner Method.", *J. Am. Chem. Soc.*, Oct. 1949, pp. 3301-3303, vol. 71.
Ibrahim et al., "Facile Approach for the Selective Glycodisation of Cyclic Asymmetric Amides and Thioamides.", *Carbohydrate Letters*, 1996, pp. 425-432, vol. 1.
Ibrahim et al., "Selective Synthesis and Structure of 2-N- and 3-S-Glucosyl-1,2,4-Triazoles of Potential Biological Interest.", *Carbohydrate Letters*, 1999, pp. 331-338, vol. 3(5).
Idris et al., "Sodium-glucose co-transporter-2 inhibitors: an emerging new class of oral antidiabetic drug.", *Diabetes, Obesity and Metabolism*, 2009, pp. 79-88, vol. 11(2), GB, XP007915350.
Isaji, M., "Sodium-glucose cotransporter inhibitor for diabetes." *Current Opinion in Investigational Drugs*, 2007, pp. 285-292, vol. 8(4).
Jain et al., "Polymorphism in Pharmacy.", *Indian Drugs*, 1986, pp. 315-329, vol. 23(6).
Kaelin et al., "General Strategies for the Synthesis of the Major Classes of C-aryl Glycosides.", *J. Am. Chem. Soc.*, 2001, pp. 6937-6938, vol. 123.
Kahn et al., "Normalization of Blood Glucose in Diabetic Rats with Phlorizin Treatment Reverses Insulin-resistant Glucose Transport in Adipose Cells without Restoring Glucose Transporter Gene Expression.", *Journal of Clinical Investigation*, 1991, pp. 561-570, vol. 87.
Kanai et al., "The Human Kidney Low Affinity Na+/Glucose Cotransporter SGLT2: Delineation of the Major Renal Reabsorptive Mechanism for D-Glucose.", *J. Clin. Invest.*, Jan. 1994, pp. 397-404, vol. 93.
Kasahara et al., "A missense mutation in the Na+/glucose cotransporter gene SGLT1 in a patient with congenital glucose-galactose malabsorption: normal trafficking but inactivation of the mutant protein.", *Biochimica et Biophysics Acta*, 2001, pp. 141-147, vol. 1536.
Katz et al., "Quantitative Insulin Sensitivity Check Index: A Simple, Accurate Method for Assessing Insulin Sensitivity in Humans.", *J. Of Clin. Endocrinology & Metabolism*, 2000, pp. 2040-2410, vol. 85(7).
Ketcha et al., "Synthesis of Alyl-Substituted N-Protected Indoles via Acylation and Reductive Deoxygenation1." *J. Org. Chem.*, 1989, pp. 4350-4356, vol. 54.
Khan et al, "Reactions of Phenyl-Substituted Heterocyclic Compounds—II. Nitrations and Brominations of 1-Phenylpyrazole Derivatives.", *Canadian Journal of Chemistry*, 1963, pp. 1540-1547, vol. 41.
Kipnes, M., "Dapagliflozin: an emerging treatment option in type 2 diabetes.", *Expert Opinion Invest. Drugs*, 2009, pp. 327-334, vol. 18(3).
Kitagawa, K., et al., "Halogen—Magnesium Exchange via Trialkylmagnesates for the Preparation of Aryl- and Alkenylmagnesium Reagents.", *Angew. Chem. Int. Ed.*, 2000, pp. 2481-2493, vol. 39(14).
Klapars et al., "Copper-Catalyzed Halogen Exchange in Aryl Halides: An Aromatic Finkelstein Reaction.", *J. Am. Chem. Soc.*, 2002, pp. 14844-14845, vol. 124(50).
Knochel, P., et al., *Organic Reactions*, vol. 58, Chapter 2: *Preparation and Application of Functionalized Orcianozinc Compounds.*, 2001, pp. 417-490, Edited by L. E. Overman, et. al., John Wiley &Sons, Inc., Publishers.
Komoroski et al., "Dapagliflozin, a Novel SGLT2 Inhibitor, Induces Dose-Dependent Glucosuria in Healthy Subjects.", *Nature*, May 2009, pp. 520-526, vol. 85(5).
Lee et al., "Recent Advances in Aryl C-Glycoside Synthesis.", *Current Topics in Medicinal Chemistry*, 2005, pp. 1333-1350, vol. 5.
Lee et al., "Synthesis and in Vitro Activity of Novel Isoxazolyl Tetrahydropyridinyl Oxazolidinone Antibacterial Agents.", *Bioorcianic & Medicinal Chemistry Letters*, 2003, pp. 4117-4120, vol. 13.
Lieberman et al., "Pharmaceutical Dosage Forms.", Second Edition, 1990, Marcel Dekker Inc., pp. 462-472, vol. 2.
Lin et al., "Syntheses of Guanidinoglycosides with the Inventive use of Mitsunobu Conditions and 1, 8-Diazabicyclo[5.4.0]undec-7-ene.", *Synthesis*, 2003, pp. 255-261, No. 2.
Link et al., "A method for preparing C-glycosides related to phlorizin.", *Tetrahedron Letters*, 2000, pp. 9213-9217, vol. 41.

(56) References Cited

OTHER PUBLICATIONS

Lipscombe et al., "Trends in diabetes prevalence, incidence, and mortality in Ontario, Canada 1995-2005: a population-based study.", Lancet, 2007, vol. 369, pp. 750-756.

Maatooq et al., "C-p-Hydroxybenzoylglycoflavones From Citrullus Colocynthis.", Phytochemistry, Jan. 1997, pp. 187-190, vol. 44(1).

Mackenzie et al., "Biophysical Characteristics of the Pig Kidney Na+/Glucose Cotransporter SGLT2 Reveal a Common Mechanism for SGLT1 and SGLT2.", J. Biol. Chem., 1996, vol. 271, pp. 32678-32683, No. 5.

Manis et al., "Metabolism of 4,4'-Methylenebis(2-chloroaniline) by Canine Liver and Kidney Slices.", Drug Metabolism and Disposition, 1986, pp. 166-174, vol. 14(2).

Marsenic, O. MD, "Glucose Control by the Kidney: An Emerging Target in Diabetes.", Am. J. of Kidney Diseases, May 2009, pp. 875-883, vol. 53(5).

Martin, S. F., "Unified Strategy for the Synthesis of C-aryl glycosides*.", Pure Appl. Chem., 2003, pp. 63-70, vol. 75(1).

Matsuda et al., "Insulin Sensitivity Indices Obtained From Oral Glucose Tolerance Testing: Comparison with the euglycemic insulin clamp.", Diabetes Care, Sep. 1999, pp. 1462-1470, vol. 22(9).

Matthews et al., "Homeostasis model assessment: insulin resistance and --cell function from fasting plasma glucose and insulin concentrations in man.", Diabetolgia, 1985, pp. 412-419, vol. 28.

Meanwell et al., "Regiospecific Functionalization of 1,3-Dihydro-2H-benzimidazol-2-one and Structurally Related Cyclic Urea Derivates.", J. Org. Chemistry, 1995, pp. 1565-1582, vol. 60(6).

Meng et al., "Discovery of Dapagliflozin: a Potent, Selective Renal Sodium-Dependent Glucose Cotransporter 2 (SGLT2) Inhibitor for the Treatment of Type 2 Diabetes.", J. Med. Chem., 2008, pp. 1145-149, vol. 51(5).

Messaoudi et al, "Synthesis and biological evaluation of oxindoles and benzimidazolinones derivatives.", European Journal of Medicinal Chemistry, 2004,pp. 453-458, vol. 39.

Mewshaw et al., "New Generation Dopaminergic Agents. 7. Heterocyclic Bioisosteres that Exploit the 3-Oh-Phenoxyethylamine D2 Template.", Bioorganic & Medicinal Chemistry Letters, 1999, pp. 2593-2598, vol. 9.

Miyaura et al., "Palladium-Catalyzed Cross-Coupling Reactions of Organoboron Compounds.", Chem. Rev., 1995, pp. 2457-2583, vol. 95(7).

Mongin, F., et al., "Deprotonation of furans using lithium magnesates.", Tetrahedron Lett., 2005, pp. 7989-7992, vol. 46.

Nishimura et al, "Tissue-specific mRNA Expression Profiles of Human ATP-binding Cassette and Solute Carrier Transporter Superfamilies.", Drug Metab. Pharmacokinet., 2005, pp. 452-477, vol. 20(6).

Nomura et al., "Discovery of canagliflozin, a novel C-glucoside with thiophene ring, as sodium dependent glucose cotransporter 2 inhibitor for the treatment of type 2 diabetes mellitus.", Journal of Med. Chem., Sep. 9, 2012, pp. 6355-6360, vol. 53(17), American Chemical Society, US, XP007915324.

Nomura, S., "Renal Sodium-Dependent Glucose Cotransporter 2 (SGLT2) Inhibitors for New Anti-Diabetic Agent.", Current Topics in Medicinal Chemistry, 2010, pp. 411-418, vol. 10(4).

Ohsumi et al. "Pyrazole-O-Glucosides as Novel Na+-Glucose Cotransporter (SGLT) Inhibitors.", Bioorganic & Medicinal Chemistry Letters, 2003, pp. 2269-2272, vol. 13.

Oku et al., "T-1095, an Inhibitor of Renal Na+-Glucose Cotransporters, May Provide a Novel Approach to Treating Diabetes.", Diabetes, Sep. 1999, pp. 1794-1800, vol. 48.

Orjales et al. "New 2-Piperazinylbenzimidazole Derivatives as 5-HT-3 Antagonists. Synthesis and Pharmacological Evaluation.", J. Med. Chem., 1997, pp. 586-593, vol. 40.

Parker et al., "Reductive Aromatization of Quinols: Synthesis of the C-Arylglycoside Nucleus of the Paulacandins and Chaetiacandin.", Organic Letters, 2000, pp. 497-499, vol. 2 (4).

Parrott, E.L., "Milling of pharmaceutical solids.", Journal of Pharmaceutical Sciences, Jun. 1974, pp. 813-829, vol. 63(6).

Patani et al., "Bioisosterism: A Rational Approach in Drug Design.", Chem. Rev., American Chemical Society, 1996, pp. 3147-3176, vol. 96.

Peng et al., "Post-transcriptional Regulation of Na+/Glucose Cotransporter (SGTL1) Gene Expression in LLC-PK1 Cells.", Journal of Biological Chemistry, 1995, pp. 20536-20542, vol. 270(35).

Perry's Chemical Engineers Handbook, Sixth Edition, 1984, pp. 21-13 to 21-19.

Pharmaceutical Sciences, Remington, 17th Ed., pp. 1585-1594 (1985).

Polshettiwar et al., "Pd-N-heterocycle carbene (NHR) organic silica: synthesis and application in carbon-carbon coupling reactions.", Tetrahedron, May 12, 2008, pp. 4637-4643, vol. 64(20), Elsevier Science Publishers, Amsterdam, NL, XP022607642.

Ramlo-Halsted B.A. & Edelman S.V., "The Natural History of Type 2 Diabetes Mellitus: Implications for Clinical Practice.", Primary Care, Dec. 1999, pp. 771-789, vol. 26(4).

Raynaud et al., "Revised Concept for the Estimation of Insulin Sensitivity From a Single Sample.", Diabetes Care, Jun. 1999, pp. 1003-1004, vol. 22(6).

Rosenstock et al., "Canagliflozin, an Inhibitor of Sodium Glucose Co-Transporter 2 (SGLT2), Improves Glycemic Control and Lowers Body Weight in Subjects with Type 2 Diabetes (T2D) on Metformin.", Diabetes, Jun. 1, 2010, pp. A21, vol. 59(supp. 1), American Diabetes Association, US, XP009139979.

Rosetti et al., "Correction of Hyperglycemia with Phlorizin Normalizes Tissue Sensitivity to Insulin in diabetic rats.", Journal of Clinical Investigation, 1987, pp. 1510-1515, vol. 79.

Rosetti et al., "Effect of Chronic Hyperglycemia on In Vivo Insulin Secretion in Partially Pancreatectomized Rats.", Journal of Clinical Investigation, 1987, pp. 1037-1044, vol. 80.

Rosetti et al., "Glucose Toxicity."; Diabetes Care, 1990, pp. 610-630, vol. 13.

Schmidt et al., "Synthese von Pyrazol-, Pyrazolo[3,4-d]pyrimidin- und 1H-1,2,4-Triazolgluconucleosiden aus Glucosehydrazonen.", Liebigs Ann. Chem., 1981, pp. 2309-2317.

Translation—Schmidt et al., "Synthese von Pyrazol-, Pyrazolo[3,4-d]pyrimidin-und 1H-1,2,4-Triazolgluconucleosiden aus Glucosehydrazonen.", Liebigs Ann. Chem., 1981, pp. 2309-2317.

Schultheiss et al., "Pharmaceutical Cocrystals and Their Physicochemical Properties.", Crystal Growth and Design, Jun. 3, 2009, pp. 2950-2967, vol. 9(6), XP55011939.

Shan et al., "The role of cocrystals in pharmaceutical science.", Drug Discovery Today, May. 1, 2008, pp. 440-446, vol. 13(9-10), Elsevier, Rahway, NJ,US, XP022649919.

Silverman, R. B., "The Organic Chemistry of Drug Design and Drug Action.", Academic Press, 1992, pp. 19-23.

Somei et al., "The First and Simple Total Synthesis of Cappariloside A[1].", Heterocycles, 2000, pp. 1573-1578, vol. 53(7).

Srogl et al., "Sulfonium salts. Participants par excellence in metal-catalyzed carbon-carbon bond-forming reactions.", Journal of the American Chemical Society, Jan. 1, 1997, pp. 12376-12377, vol. 119, American Chemical Society, US, XP002955770.

Stoner et al., "Benzylation via Tandem Grignard Reaction—Lodotrimethylsilane (TMSI) Mediated Reduction.", Tetrahedron, 1995, pp. 11043-11062, vol. 51(41).

Stumvoll et al., "Use of the Oral Glucose Tolerance Test to Assess Insulin Release and Insulin Sensitivity.", Diabetes Care, Mar. 2000, pp. 295-301, vol. 23(3).

Tanaka et al. "Solid-Phase Synthesis of—Mono-Substituted Ketones and an Application to the Synthesis of a Library of Phlorizin Derivatives.", Synlett, 2002, pp. 1427-1430, No. 9.

Thornber, C.T., "Isosterism and Molecular Modification in Drug Design.", Chem. Society Review, 1979, pp. 563-580, vol. 8.

Tilak et al, "Carcinogenesis by Thiophene Isosters of Polycyclic Hydrocarbons.", Tetrahedron, 1960, pp. 76-95, vol. 9.

Tsujihara et al., "Na+ Glucose Cotransporter (SGLT) Inhibitors as Antidiabetic Agents. 4. Synthesis and Pharmacological Properties of 4'-Dehydroxyphlorizin Derivatives Substituted on the B Ring.", Journal of Medicinal Chemistry, 1999, pp. 5311-5324, vol. 42.

Tsujihara et al., Bio Clinica, 1998, pp. 324-328, vol. 13(4), English language Abstract.

(56) References Cited

OTHER PUBLICATIONS

Turk et al., "Glucose/galactose malabsorption caused by a defect in the Na+/glucose cotransporter.", *Nature*, Mar. 1991, pp. 354-356, vol. 350.

Ueta et al., "Long-term treatment with the Na+-glucose contransporter inhibitor T1095 causes sustained improvement in hyperglycemia and prevents diabetic neuropathy in Goto-Kakizaki Rats.", *Life Sci.*, 2005, pp. 2655-2668, vol. 76(23).

Unger et al., "Hyperglycemia as an inducer as well as a consequence of impaired islet cell function and insulin resistance: implications for the management of diabetes.", *Diabetologia*, 1985, pp. 119-121, vol. 28.

Vippagunta et al., "Crystalline Solids.", *Advanced Drug Delivery Reviews*, 2001, pp. 3-26, vol. 48.

Vishweshwar et al., "Pharmaceutical co-crystals.", *Journal of Pharmaceutical Sciences*, Mar. 1, 2006, pp. 499-516, vol. 95(3), American Pharmaceutical Association, Washington, US.

Wallace et al., "Use and Abuse of Homa Modeling.", *Diabetes Care*, Jun. 2004, pp. 1487-1495, vol. 27(6).

Wang et al, "Selective monolithiation of 2,5-dibromopyridine with butyllithium.", *Tetrahedron Letters*, 2000, pp. 4335-4338, vol. 41.

Wareham et al., "Is There Really an epidemic of diabetes?", *Diabetologia*, 2005, pp. 1454-1455, vol. 48.

Washburn, W. N., "Evolution of sodium glucose co-transporter 2 inhibitors as anti-diabetic agents.", *Expert Opin. Ther. Patents*, 2009, pp. 1485-1499, vol. 19(11).

Watanabe et al., "Cyclopentyl Methyl Ether as a New and Alternative Process Solvent.", *Organic Process Research and Development*, 2007, pp. 251-258, vol. 11.

Wild et al., "Global Prevalence of Diabetes: Estimates for the year 2000 and projections for 2030.", *Diabetes Care*, May 2004, pp. 1047-1053, vol. 27(5).

Wolff, M. E. vol. 1: *Principles and Practice, Burner's Medicinal Chemistry and Drug Discovery*, 5th Edition, 1995, pp. 975-977.

Wright, E.M., "Renal Na+-glucose cotransporters.", *Am J Physiol Renal Physiol*, 2001, pp. F10-F18, vol. 280.

Wurster D.E., "Air-suspension Technique of Coating Drug Particles* A Preliminary Report.", *Journal of the American Pharmaceutical Association*, Aug. 1959, pp. 451-454, vol. 48(8).

Wurster, D.E., "Preparation of compressed tablet granulations by the air-suspension technique II.", *Journal of the American Pharmaceutical Association*, 1960, pp. 82-84, vol. 49(2).

Yang et al., "Convergent C-Glycolipid Synthesis via the Ramberg-Backlund Reaction: Active Antiproliferative Glycolipids.", *Org. Lett.* 1999, pp. 2149-2151, vol. 1913).

Yoshimura et al., "Discovery of Novel and PotenCRetinoic Acid Receptor alpha—Agonists: Synthesis and Evaluation of Benzofuranyl-pyrrole and Benzothiophenyl-pyrrole Derivatives," *J. Med. Chem.*, 2000, pp. 2929-2937, vol. 43.

Zamani et al., "Synthesis and Structure Determination of Some New N-Glycosides of 4,5-Disubstituted-1,2,4-triazole-3-thiones.", *Journal of the Chinese Chemical Society*, 2002, pp. 1041-1044, vol. 49.

Zhdanov, Y. et al., "Application of organozinc compounds in the synthesis of carbon-carbon derivatives of sugars.", 2001, Database CA (online), Chemical Abstracts Service, Columbus, Ohio, USA, XP002612365.

Translation—Zhdanov, Y. et al., "Application of organozinc compounds in the synthesis of carbon-carbon derivatives of sugars.", 2001, Database CA (online), Chemical Abstracts Service, Columbus, Ohio, USA, XP002612365.

Zhou, F. Y., "The Synthesis and Characterization of 1-Benzyl-3-N-(Beta-D-glucosie-1-yl)-4-fluorouracil.", *Hecheng Huaxue*, 2001, pp. 272-274, vol. 9(3).

Jianqun, et al., "Recent advances in palladium catalysts for aryl chlorides coupling reaction", *Industrial Catalysis*, Jul. 31, 2005, pp. 29-44, vol. 13(7).

Zhiyin, et al., "Cross-coupling reaction of Grignard reagent with thiophenyl halides by using nickel phosphine as catalyst and the synthesis of α-terthienyl", *Huaxue Shiji*, Dec. 31, 1995, pp. 289-290, vol. 17(5).

Byrn et al., "Pharmaceutical Solids: A Strategic Approach to Regulatory Considerations.", *Pharml. Res.*, 1995, pp. 945-954, vol. 12(7).

Bavin, M., "Process Development: Polymorphism in Process Development.", *Chemistry & Industry*, 1989, pp. 527-529, vol. 16.

Kozikowski et al., "Organometallics in Organic Synthesis. Applications of a New Diorganozinc Reaction to the Synthesis of C-Glycosyl Compounds With Evidence for an Oxonium-Ion Mechanism*.", *Carbohydrate Research*, 1987, pp. 109-124, vol. 171.

Asahara et al. *Handbook of Solvents*, K.K. Kodansah., Sep. 1, 1985, Sixth Printing, pp. 47-51, Tokyo, JP.

Clinical Trial NTC00642278, Clinical Trials.gov/archive/NTC00642278, View of Trial on Jun. 20, 2009.

Clinical Trial, "An Efficacy, Safety, and Tolerability Study of Canagliflozin (JNJ-28431754) in Patients With Type 2 Diabetes.", Clinical Trial NTC00642278, accessed Mar. 20, 2015.

Lotfi et al., "Case Study: Weight Loss in a Patient with Type 2 Diabetes: Challenges of Diabetes Management.", *Obesity*, Apr. 2015, pp. S11-S12, vol. 23(Supp. 1), XP002764434.

Rosenthal et al., "Canagliflozin: a sodium glucose co-transporter 2 inhibitor for the treatment of type 2 diabetes mellitus.", *Annals of the New Your Academy of Sciences*, Aug. 25, 2015, pp. 28-43, vol. 1358, XP002764435.

Clinical Trial NCT02243202, "Effects of Co-administration of Canagliflozin 300 mg and Phentermine 15 mg With Placebo in the Treatment of Non-Diabetic Overweight and Obese Participants", clinicaltrials.gov, Aug. 10, 2015, XP02764436, Retrieved from Internet: URL:https://clinicaltrials.gov/archive/NCT02243202/2015_08_10[retrieved onNov. 16, 2016], the whole document, XP002764436.

Cosentino et al., "Phentermine and topiramate for the management of obesity: a review.", *Drug Design, Development and Therapy*, Apr. 1, 2013, pp. 267-278, vol. 7., XP055320698.

Taylor et al., "New and Emerging Pharmacologic Therapies for Type 2 Diabetes, Dyslipidemia, and Obesity.", *Clinical Therapeutics*, Jan. 2013, pp. A3-A17, vol. 35(1), XP05532084.

Clinical Trial NCT02243202, "Effects of Co-administration of Canagliflozin 300 mg and Phentermine 15 mg With Placebo in the Treatment of Non-Diabetic Overweight and Obese Participants", clinicaltrials.gov, Jun. 16, 2016, XP02764436, Retrieved from Internet:URL:https://clinicaltrials.gov/ct2/show/results/NCT02243202?term=NCT02243202&rank=1[retrieved onNov. 16, 2016], the whole document, XP002764437.

Morrisson, A., "Canagliflozin, Phentermine Combo Provides Greater Weight Loss vs Placebo for Obese Adults.", *DGnews*, Jun. 16, 2016, Retrieved from the internet: URL:http://dgnews.docguide.com/canagliflozin-phentermine-combo-provides-greater-weight-loss-vs-placebo-obese-adults[retrieved on Nov. 16, 2016], the whole document, XP002764438.

Edwards et al., "D-Beta-Hydroxybutyrate extends lifespan in C. elegans.", *Aging*, 2014, pp. 621-644, vol. 6(8).

Ford et al., "Prevalence of the Metabolic Syndrome Among US Adults: Findings From the Third National Health and Nutrition Examination Survey.", *JAMA*, 2002, pp. 356-359, vol. 287(3).

Kimura et al., "Short-chain fatty acids and ketones directly regulate sympathetic nervous system via GPR41.", *Proc. Natl. Acad. Sci.*, 2011, pp. 8030-8035, vol. 108(19).

Laaksonen et al., "Metabolic Syndrome and Development of Diabetes Mellitus: Application and Validation of Recently Suggested Definitions of the Metabolic Syndrome in a Prospective Cohort Study.", American Journal of Epidemiology, 2002, pp. 1070-1077, vol. 156.

Magee et al., "Is hyperfiltration associated with the future risk of developing diabetic nephropathy? A meta-analysis.", Diabetologia, 2009, pp. 691-697, vol. 52.

Meigs et al., "The Natural History of Progression From Normal Glucose Tolerance to Type 2 Diabetes in the Baltimore Longitudinal Study of Aging.", Diabetes, Jun. 2003, pp. 1475-1484, vol. 52.

Newman et al., "Ketone bodies as signaling metabolites." *Trends Endocrinology and Metabolism*, 2014, pp. 42-52, vol. 25(1).

Shimazu et al., "Suppression of Oxidative Stress by Beta-Hydroxybutyrate, an Endogenous Histone Deacetylase Inhibitor.", *Science*, Jan. 11, 2013, pp. 211-214, vol. 339.

(56) References Cited

OTHER PUBLICATIONS

Taggart et al., "D-Beta-Hydroxybutyrate inhibits adipocyte lipolysis via the nicotinic acid receptor PUMB-G.", *J. Biol. Chem.*, 2005, pp. 26649-26652, vol. 280(29).
Youm et al., "The ketone metabolite beta-hydroxybutyrate blocks NLRP3 inflammasome-mediated inflammatory disease.", *Nature Medicine*, 2015, pp. 263-269, vol. 21(3).
Executive Summary of the Third Report of the National Cholesterol Education Program (NCEP) Expert Panel on Detection, Evaluation, and Treatment of High Blood Cholesterol in Adults (Adult Treatment Panel III), *JAMA: Journal of the American Medical Association*, 2001, pp. 2486-2497, vol. 285(19).
World Health Organization, "Obesity: Preventing and Managing the Global Epidemic: Report on a WHO Consultation.", *World Health Organ Tech Rep Ser.*, 2000, pp. i-xii, 1-253, 894.
Austin P.C., et al., "A brief note on overlapping confidence intervals" *Journal of Vascular Surgery*, 2002, pp. 194-195, vol. 36.
Jabbour et al., "Effects of exenatide once weekly plus dapagliflozin, exenatide once weekly, or dapagliflozin, added to metformin monotherapy, on body weight, systolic blood pressure, and triglycerides in patients with type 2 diabetes in the DURATION-8 study.", *Diabetes Obes Metab.*, 2018, pp. 1515-1519, vol. 20.
Schenker, N., et al., "On judging the significance of differences by examining the overlap between confidence intervals", *The American Statistician*, 2001, pp. 182-186, vol. 55.
International Search Report of the International Searching Authority relating to corresponding International Patent Application No. PCT/US2016/051435, filed Sep. 13, 2016. dated Dec. 5, 2016.
Written Opinion of the International Searching Authority relating to corresponding International Patent Application No. PCT/US2016/051435, filed Sep. 13, 2016, dated Dec. 5, 2016.
Apovian et al, "Pharmacological Management of Obesity: An Endocrine Society Clinical Practice Guideline.", J Clin Endocrinol Metab, Feb. 2015, pp. 342-364, vol. 100(2).
Bays et al., "Canagliflozin: Effects in Overweight and Obese Subjects Without Diabetes Mellitus.", Obesity, Apr. 2014, pp. 1042-1049, vol. 22(4).
Haneda et al., "Topics II. Recent Topics in Treatment. Drug Therapy of Obesity.", Japan Pharmaceutical Society, 2015, pp. 735-741, vol. 104, Translation only.
Hendricks et al., "Blood Pressure and Heart Rate Effects, Weight Loss and Maintenance During Long-Term Phentermine Pharmacotherapy for Obesity.", Obesity, Dec. 2011, pp. 2351-2360, vol. 19(12).
Cefalu et al., "Effects of Canagliflozin on body weight and relationship to $HbA_{1c}$ and blood pressure changes in patients with type 2 diabetes.", Diabetologia, 2015, pp. 1183-1187, vol. 58(6).

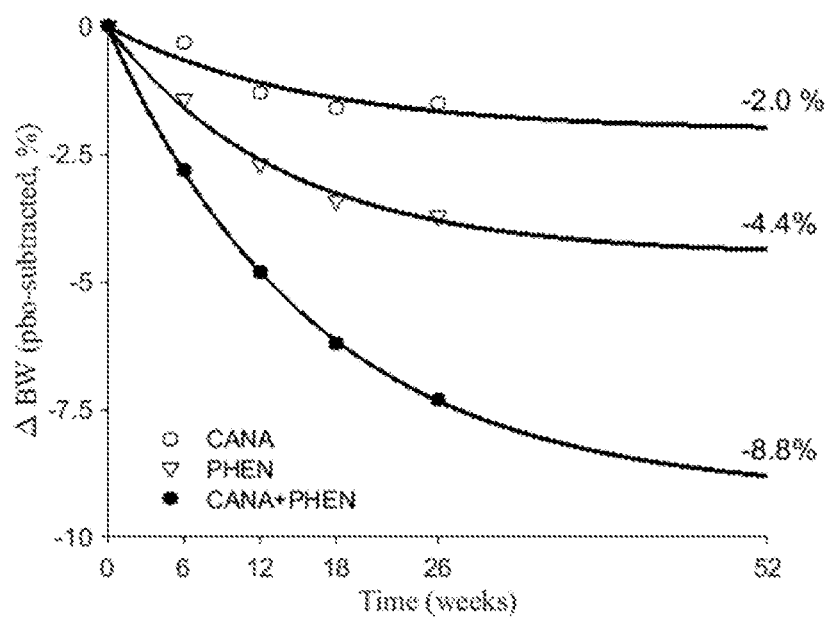
Mean placebo-subtracted weight loss (measured at 0-26 Weeks, extrapolated to 52 Weeks) for Canagliflozin, Phentermine and Combiantion Therapy

CO-THERAPY COMPRISING CANAGLIFLOZIN AND PHENTERMINE FOR THE TREATMENT OF OBESITY AND OBESITY RELATED DISORDERS

CROSS-REFERENCE TO RELATED APPLICATIONS

This Application is a continuation of U.S. patent application Ser. No. 16/245,682, filed on Jan. 11, 2019, which is a continuation of U.S. patent application Ser. No. 15/262,038, filed Sep. 1, 2016, which claims priority to U.S. Provisional Patent Application No. 62/218,842, filed Sep. 15, 2015, and U.S. Provisional Patent Application No. 62/306,110, filed Mar. 10, 2016, the disclosures of which are hereby incorporated by reference in their entireties.

FIELD OF THE INVENTION

The present invention is directed to the use of co-therapy comprising administration of canagliflozin and phentermine for the treatment of obesity and obesity related disorders. More particularly, the present invention is directed to co-therapy for treating obesity, for promoting weight loss and/or for suppressing appetite; for treating, delaying, slowing the progression of and/or preventing metabolic disorders (including for example Type 2 diabetes mellitus); for treating, delaying, slowing the progression of and/or preventing renal or fatty liver disorders (including for example NASH, NAFLD, etc.); for treating, delaying, slowing the progression of and/or preventing sleep disorders (including for example sleep apnea); for providing cardiovascular protection; for treating, delaying, slowing the progression of and/or preventing cardiovascular events (including major adverse cardiac events (MACE) such as myocardial infarction, unstable angina, cardiovascular death, revascularization, fatal or non-fatal cerebrovascular accident, peripheral arteriopathy, aortic events, hospitalization due to congestive heart failure, etc.); and/or for extending or prolonging life span.

BACKGROUND OF THE INVENTION

Obesity is a state of excess adipose tissue mass. Although often viewed as equivalent to increased body weight, this need not be the case-lean but very muscular individuals may be overweight by arbitrary standards without having increased adiposity. Body weights are distributed continuously in populations, so that a medically meaningful distinction between lean and obese is somewhat arbitrary. Obesity is therefore more effectively defined by assessing its linkage to morbidity or mortality.

Although not a direct measure of adiposity, the most widely used method to gauge obesity is the body mass index (BMI), which is equal to weight/height$^2$ (in kg/m$^2$). Other approaches to quantifying obesity include anthropometry (skin-fold thickness), densitometry (underwater weighing), computed tomography (CT) or magnetic resonance imaging (MRI), and electrical impedance. Using data from the Metropolitan Life Tables, BMIs for the midpoint of all heights and frames among both men and women range from 19 to 26 kg/m$^2$; at a similar BMI, women have more body fat than men. Based on unequivocal data of substantial morbidity, a BMI of 30 is most commonly used as a threshold for obesity in both men and women. Large-scale epidemiologic studies suggest that all-cause, metabolic, and cardiovascular morbidity begin to rise (albeit at a slow rate) when BMIs are ≥25, suggesting that the cut-off for obesity should be lowered. Some authorities use the term overweight (rather than obese) to describe individuals with BMIs between 25 or 27 and 30. A BMI between 25 and 30 should be viewed as medically significant and worthy of therapeutic intervention, especially in the presence of risk factors that are influenced by adiposity, such as hypertension and glucose intolerance.

Recent data from the National Health and Nutrition Examination Surveys (NHANES) show that the percent of the American adult population with obesity (BMI>30) has increased from 14.5% (between 1976 and 1980) to 22.5% (between 1998 and 1994). As many as 50% of U.S. adults ≥20 years of age were overweight (defined as BMI>25) between the years of 1998 and 1991. Because substantial health risks exist in many individuals with BMI between 25 and 30, the increasing prevalence of medically significant obesity raises great concern. Obesity is more common among women and in the poor; the prevalence in children is also rising at a worrisome rate.

Obesity has major adverse effects on health. Morbidly obese individuals (>200% ideal body weight) have as much as a twelve-fold increase in mortality. Mortality rates rise as obesity increases, particularly when obesity is associated with increased intra-abdominal fat. It is also apparent that the degree to which obesity affects particular organ systems is influenced by susceptibility genes that vary in the population. Obese individuals have a 50-100% increased risk of premature death from all causes compared to individuals with normal body weight. Over 300,000 deaths a year in the United States may be attributable to obesity.

Patients with obesity also have a higher chance of developing insulin resistance or glucose intolerance, which can progress to the development of type-2 diabetes. There is also a higher probability of high blood pressure, sexual dysfunction, headaches, depression and sleep apnea.

Diabetes mellitus is a medical term for the presence of elevated blood glucose. People with diabetes either don't produce insulin, produce too little insulin or do not respond to insulin, resulting in the build up of glucose in the blood. The most common form of diabetes is Type 2 diabetes, once referred to as adult onset diabetes or non-insulin dependent diabetes (NIDDM), which may account for >90% of diabetes in adults. However, as the younger population becomes increasingly overweight or obese, Type 2 diabetes is becoming more prevalent in teens and children. Diabetes may also refer to gestational diabetes, Type 1 diabetes or autoimmune diabetes, once referred to as juvenile onset diabetes and type 1½ diabetes, also referred to as latent-autoimmune diabetes in adults or LADA. Diabetes may occur because of poor dietary habits or lack of physical activity (e.g., sedentary lifestyle), genetic mutations, injury to the pancreas, drug (e.g., AIDS therapies) or chemical (e.g., steroid) exposure or disease (e.g., cystic fibrosis, Down syndrome, Cushing's syndrome). Two rare types of genetic defects leading to diabetes are termed maturity-onset diabetes of the young (MODY) and atypical diabetes mellitus (ADM).

Type II diabetes mellitus (non-insulin-dependent diabetes mellitus or NIDDM) is a metabolic disorder involving disregulation of glucose metabolism and insulin resistance, and long-term complications involving the eyes, kidneys, nerves, and blood vessels. Type II diabetes mellitus usually develops in adulthood (middle life or later) and is described as the body's inability to make either sufficient insulin (abnormal insulin secretion) or its inability to effectively use insulin (resistance to insulin action in target organs and tissues). More particularly, patients suffering from Type II diabetes mellitus have a relative insulin deficiency. That is, in these patients, plasma insulin levels are normal to high in absolute terms, although they are lower than predicted for the level of plasma glucose that is present.

Type II diabetes mellitus is characterized by the following clinical signs or symptoms: persistently elevated plasma glucose concentration or hyperglycemia; polyuria; polydipsia and/or polyphagia; chronic microvascular complications such as retinopathy, nephropathy and neuropathy; and macrovascular complications such as hyperlipidemia and hypertension which can lead to blindness, end-stage renal disease, limb amputation and myocardial infarction.

Syndrome X, also termed Insulin Resistance Syndrome (IRS), Metabolic Syndrome, or Metabolic Syndrome X, is a disorder that presents risk factors for the development of Type II diabetes mellitus and cardiovascular disease including glucose intolerance, hyperinsulinemia and insulin resistance, hypertriglyceridemia, hypertension and obesity.

The diagnosis of Type II diabetes mellitus includes assessment of symptoms and measurement of glucose in the urine and blood. Blood glucose level determination is necessary for an accurate diagnosis. More specifically, fasting blood glucose level determination is a standard approach used. However, the oral glucose tolerance test (OGTT) is considered to be more sensitive than fasted blood glucose level. Type II diabetes mellitus is associated with impaired oral glucose tolerance (OGT). The OGTT thus can aid in the diagnosis of Type II diabetes mellitus, although generally not necessary for the diagnosis of diabetes (Emancipator K, Am J Clin Pathol 1999 November; 112(5):665-74; Type 2 Diabetes Mellitus, Decision Resources Inc., March 2000). The OGTT allows for an estimation of pancreatic beta-cell secretory function and insulin sensitivity, which helps in the diagnosis of Type II diabetes mellitus and evaluation of the severity or progression of the disease (e.g., Caumo A, Bergman R N, Cobelli C, J Clin Endocrinol Metab 2000, 85(11):4396-402). More particularly, the OGTT is extremely helpful in establishing the degree of hyperglycemia in patients with multiple borderline fasting blood glucose levels that have not been diagnosed as diabetics. In addition, the OGTT is useful in testing patients with symptoms of Type II diabetes mellitus where the possible diagnosis of abnormal carbohydrate metabolism has to be clearly established or refuted.

Thus, impaired glucose tolerance is diagnosed in individuals that have fasting blood glucose levels less than those required for a diagnosis of Type II diabetes mellitus, but have a plasma glucose response during the OGTT between normal and diabetics. Impaired glucose tolerance is considered a prediabetic condition, and impaired glucose tolerance (as defined by the OGTT) is a strong predictor for the development of Type II diabetes mellitus (Haffner S M, Diabet Med 1997 August; 14 Suppl 3:S12-8).

Type II diabetes mellitus is a progressive disease associated with the reduction of pancreatic function and/or other insulin-related processes, aggravated by increased plasma glucose levels. Thus, Type II diabetes mellitus usually has a prolonged prediabetic phase and various pathophysiological mechanisms can lead to pathological hyperglycemia and impaired glucose tolerance, for instance, abnormalities in glucose utilization and effectiveness, insulin action and/or insulin production in the prediabetic state (Goldberg R B, Med Clin North Am 1998 July; 82(4):805-21).

The prediabetic state associated with glucose intolerance can also be associated with a predisposition to abdominal obesity, insulin resistance, hyperlipidemia, and high blood pressure, that is, Syndrome X (Groop L, Forsblom C, Lehtovirta M, Am J Hypertens 1997 September; 10(9 Pt 2):172S-180S; Haffner S M, J Diabetes Complications 1997 March-April; 11(2):69-76; Beck-Nielsen H, Henriksen J E, Alford F, Hother-Nielson O, Diabet Med 1996 September; 13(9 Suppl 6):S78-84).

Thus, defective carbohydrate metabolism is pivotal to the pathogenesis of Type II diabetes mellitus and impaired glucose tolerance (Dinneen S F, Diabet Med 1997 August; 14 Suppl 3:S19-24). In fact, a continuum from impaired glucose tolerance and impaired fasting glucose to definitive Type II diabetes mellitus exists (Ramlo-Halsted B A, Edelman S V, Prim Care 1999 December; 26(4):771-89).

Early intervention in individuals at risk to develop Type II diabetes mellitus, focusing on reducing the pathological hyperglycemia or impaired glucose tolerance may prevent or delay the progression towards Type II diabetes mellitus and associated complications and/or Syndrome X. Therefore, by effectively treating impaired oral glucose tolerance and/or elevated blood glucose levels, one can prevent or inhibit the progression of the disorder to Type II diabetes mellitus or Syndrome X.

Kidneys are bean-shaped organs, located near the middle of the back. Inside each kidney about a million tiny structures called nephrons filter blood. They remove waste products and extra water, which become urine. Damage to the nephrons represents an important form of kidney disease. This damage may leave kidneys unable to remove wastes. Some damage, e.g. damage related to hyperfiltration can occur slowly over years, initially often without obvious symptoms.

The 'hyperfiltrative hypothesis' implies that the excess demand on a limited renal reserve produces adaptive and ultimately pathologic changes in the kidney which finally lead to 'nephron exhaustion'. At the single-nephron level, hyperfiltration is hypothesized to be an early link in the chain of events that lead from intraglomerular hypertension to albuminuria and, subsequently, to reduced Glomerular Filtration Rate (GFR). Based on this hyperfiltration therefore represents a risk for subsequent renal injury and could be classified as an early manifestation of renal pathology often referred to as the hyperfiltrative stage. Such renal hyperfiltration can lead to early glomerular lesions and to microalbuminuria, which itself can lead to macroalbuminuria and to end-stage renal disease.

The influence of hyperfiltration on renal function decline has been most thoroughly evaluated in kidney transplant recipients and donors, and in patients with a single kidney removed for acquired renal disease, but also in patients with diabetes mellitus (Magee et al. Diabetologia 2009; 52: 691-697). In theory, any reduction in functional nephron number will lead to adaptive glomerular hyperfiltration whether induced genetically, surgically, or by acquired renal disease. Moreover, hyperfiltration has been shown to occur in certain pathophysiologic conditions even when renal mass is intact, e.g. in diabetes. Therefore, there is a medical need for interventions with a good efficacy with regard to renal hyperfiltrative injury.

Creatinine is a breakdown product of creatine phosphate in muscle tissue, and is usually produced at a constant rate in the body. Serum creatinine is an important indicator of renal health, because it is an easily measured byproduct of muscle metabolism that is excreted unchanged by the kidneys. Creatinine is removed from the blood chiefly by the kidneys, primarily by glomerular filtration, but also by proximal tubular secretion. Little or no tubular reabsorption of creatinine occurs. If the filtration in the kidney is deficient, creatinine blood levels rise. Therefore, creatinine levels in blood and urine may be used to calculate the creatinine clearance (CrCl), which correlates with the glomerular filtration rate (GFR). Blood creatinine levels may also be used alone to estimate the GFR (eGFR). The GFR is clinically important because it is a measurement of renal function. An alternate estimation of renal function can be made when interpreting the blood (plasma) concentration of creatinine along with that of urea. The BUN-to-creatinine ratio (the ratio of blood urea to creatinine) can indicate other problems besides those intrinsic to the kidney; for example, a urea level raised out of proportion to the creatinine may indicate a pre-renal problem such as volume depletion.

A rise in blood creatinine level is observed only with marked damage to functioning nephrons. An estimation of kidney function is given by calculating the estimated glomerular filtration rate (eGFR). eGFR can be accurately calculated using serum creatinine concentration. The typical human reference ranges for serum creatinine are 0.5 to 1.0 mg/dl (about 45-90 μmol/l) for women and 0.7 to 1.2 mg/dl (60-110 μmol/l) for men. The trend of serum creatinine levels over time is generally more important than absolute creatinine level.

Creatinine levels may increase modestly when an ACE inhibitor (ACEi) or angiotensin II receptor antagonist (or angiotensin receptor blocker, ARB) is taken. Using both an ACE inhibitor and ARB concomitantly will increase creatinine levels to a greater degree than either of the two drugs would individually. An increase of <30% is to be expected with ACE inhibitor or ARB use.

Albuminuria is a condition, where albumin is present in the urine. In healthy individuals, albumin is filtered by the kidneys. When the kidneys do not properly filter large molecules (such as albumin) from the urine, albumin is excreted in urine and is typically a sign of kidney damage or excessive salt intake. Albuminuria can also occur in patients with long-standing diabetes mellitus, either Type I (1) or Type II (2) diabetes mellitus. Urine albumin may be measured by dipstick or as direct measure of the amount of protein excreted in total volume of urine collected over a 24 hour period Microalbuminuria, occurs when the kidney leaks small amounts of albumin into the urine, as a result of an abnormally high permeability for albumin in the renal glomerulus. Microabuminuria as a condition of diabetic nephropathy is indicated when urine albumin levels are in the range of 30 mg to 300 mg in a 24 hour period.

An alternate measure of microalbuminuria is creatinine levels and the ratio of albumin to creatinine in serum. The albumin/creatinine ratio (ACR) and microalbuminuria are defined as ACR ≥3.5 mg/mmol (female) or ≥2.5 mg/mmol (male), or, with both substances measured by mass, as an ACR between 30 μg albumin/mg creatinine and 300 μg albumin/mg creatinine.

Microalbuminuria may be an important prognostic marker for the development and progression of kidney disease, particularly in patients with diabetes mellitus or hypertension. Microalbuminuria is also an indicator of subclinical cardiovascular disease, a marker of vascular endothelial dysfunction and a risk factor for venous thrombosis.

Diabetic nephropathy is one of the microvascular complications of diabetes mellitus and is characterized by persistent albuminuria and a progressive decline in renal function. Hyperglycemia is an important contributor to the onset and progression of diabetic nephropathy.

The clinical progression of diabetic nephropathy in patients with T1DM (Type 1 Diabetes Mellitus) is well characterized. Initially, hyperfiltration accompanied by increases in glomerular filtration rate (GFR) and increased renal plasma flow is seen. A meta-analysis found that the presence of hyperfiltration in patients with T1DM more than doubled the risk of developing micro- or macroalbuminuria. This phase is followed by reductions in GFR and the development of microalbuminuria, defined as urinary albumin excretion of ≥30 mg/day (or 20 μg/min) and <300 mg/24 h (or <200 μg/min), which may be accompanied by increases in blood pressure. Later in the progression of the disease as GFR continues to decline, overt proteinuria (i.e., macroalbuminuria), defined as urinary albumin excretion of >300 mg/day ensues and is associated with worsening hypertension. Eventually, ESKD (End Stage Kidney Disease) progresses, leading to the need for renal replacement therapy.

In patients with Type 2 Diabetes Mellitus (T2DM), the clinical progression is variable, primarily due to multiple renal insults, including not only hyperglycemia, but also vascular pathology resulting in ischemic renal injury. However, other common features are likely to contribute to renal injury in patients with T2DM include hyperfiltration at the level of the single nephron, proximal tubular glucotoxicity, and a stimulus for tubular cell growth as a result of enhanced sodium coupled glucose transport into tubular cells.

Studies have demonstrated that albuminuria is a biomarker for predicting progression of diabetic nephropathy and is a cardiovascular (CV) risk factor. When compared with patients with normo-albuminuria and estimated glomerular filtration rate (eGFR) ≥90 mL/min/1.73 m$^2$, patients with both macroalbuminuria and eGFR <60 mL/min/1.73 m$^2$ were at 5.9-fold higher risk (95% Cl 3.5 to 10.2) for cardiovascular death and 22.2-fold higher risk (95% Cl 7.6 to 64.7) for experiencing ESKD, and subjects with macroalbuminuria and reduced eGFR (ie, <60 mL/min/1.73 m$^2$) were nearly 6 times more likely to experience a composite renal event (i.e., death as a result of kidney disease, requirement for dialysis or transplantation, or doubling of serum creatinine. See, e.g., J Am Soc Nephrol 20(8):1813-1821, 2009. A close link between the degree of albuminuria and CV disease has also been demonstrated in the RENAAL study, showing that patients with high baseline urinary albumin/creatinine ratio (ACR) (≥3 g/g) had a 1.2-fold (95% Cl, 1.54 to 2.38) higher risk of a composite of myocardial infarction (MI), stroke, first hospitalization for heart failure or unstable angina, coronary or peripheral revascularization, or CV death, and a 2.7-fold (95% Cl, 1.94 to 3.75) higher risk of heart failure compared with patients with an ACR <1.5 g/g. Increased urinary albumin excretion and reduced eGFR are also independently associated with the risk for both cardiovascular and kidney outcomes in patients with T2DM, without evidence for an interaction between these risk factors. Moderately increased albuminuria also has been associated with an increase in renal disease progression.

In summary, the magnitude of albuminuria positively correlates with the development of ESKD and adverse CV outcomes. Treatment-related reductions in albuminuria in patients with T2DM and albuminuria using agents acting by a hemodynamic mechanism (i.e., ACEi and ARBs) are correlated with reductions in the progression of diabetic nephropathy and in the incidence of adverse CV outcomes. Thus, agents acting by a unique hemodynamic mechanism to reduce albuminuria beyond that seen with other antihypertensive or antihyperglycemic agents and which are additive to agents disrupting the renin-angiotensin system may exert reno-protective effects and possibly reduce adverse CV outcomes in diabetic nephropathy.

Fatty liver, also known as fatty liver disease (FLD), is a reversible condition wherein large vacuoles of triglyceride fat accumulate in liver cells via the process of steatosis (i.e., abnormal retention of lipids within a cell). Accumulation of fat may also be accompanied by a progressive inflammation of the liver (hepatitis), called steatohepatitis. By considering the contribution by alcohol, fatty liver may be termed alcoholic steatosis or non-alcoholic fatty liver disease (NAFLD), and the more severe forms as alcoholic steatohepatitis (part of alcoholic liver disease) and non-alcoholic steatohepatitis (NASH).

Non-alcoholic fatty liver disease (NAFLD) is one cause of a fatty liver, occurring when fat is deposited (steatosis) in the liver. NAFLD is considered to cover a spectrum of disease activity. This spectrum begins as fatty accumulation in the liver (hepatic steatosis). A liver can remain fatty without disturbing liver function, but by varying mechanisms and possible insults to the liver may also progress to become NASH, a state in which steatosis is combined with inflammation and fibrosis. Non-alcoholic steatohepatitis (NASH) is a progressive, severe form of NAFLD. Over a 10-year period, up to 20% of patients with NASH will develop cirrhosis of the liver, and 10% will suffer death related to liver disease. The exact cause of NAFLD is still unknown, however, both obesity and insulin resistance are thought to play a strong role in the disease process. The exact reasons and mechanisms by which the disease progresses from one stage to the next are not known.

NAFLD has been linked to insulin resistance (IR) and the metabolic syndrome (MS). As the renin-angiotensin system (RAS) plays a central role in insulin resistance, and subsequently in NAFLD and NASH, an attempt to block the deleterious effects of RAS overexpression has been proposed a target for treatment. While many potential therapies tested in NASH target only the consequences of this condition, or try to "get rid" of excessive fat, angiotensin receptor blockers (ARBs) may act as a tool for correction of the various imbalances that act in harmony in NASH/NAFLD. Indeed, by inhibiting RAS the intracellular insulin signaling pathway may be improved, resulting in better control of adipose tissue proliferation and adipokine production, as well as more balanced local and systemic levels of various cytokines. At the same time, by controlling the local RAS in the liver fibrosis may be prevented and the cycle that links steatosis to necroinflammation slowed down. (GEORGESCU, E. F., in *Advances in Therapy,* 2008, pp 1141-1174, Vol. 25, Issue 11)

Sleep apnea is a sleep disorder characterized by pauses in breathing or instances of shallow or infrequent breathing during sleep. Each pause in breathing, called an apnea, can last for several seconds to several minutes, and may occur, by definition, at least 5 times in an hour. Similarly, each abnormally shallow breathing event is called a hypopnea. Sleep apnea is classified as a dyssomnia, meaning abnormal behavior or psychological events occur during sleep. When breathing is paused, carbon dioxide builds up in the bloodstream. Chemoreceptors in the blood stream note the high carbon dioxide levels. The brain is signaled to wake the person sleeping and breathe in air. Breathing normally will restore oxygen levels and the person will fall asleep again. Sleep apnea is often diagnosed with an overnight sleep test or "sleep study".

There are three forms of sleep apnea: central (CSA), obstructive (OSA) and complex or mixed sleep apnea (i.e., a combination of central and obstructive) constituting 0.4%, 84%, and 15% of cases, respectively. In CSA, breathing is interrupted by a lack of respiratory effort; in OSA, breathing is interrupted by a physical block to airflow despite respiratory effort, and snoring is common. According to the NIH, 12 million Americans have OSA. There are more cases of sleep apnea still because people either do not report the condition or do not know they have sleep apnea.

Regardless of type, an individual with sleep apnea is rarely aware of having difficulty breathing, even upon awakening. Sleep apnea is recognized as a problem by others witnessing the individual during episodes or is suspected because of its effects on the body. Symptoms may be present for years (or even decades) without identification, during which time the person may become conditioned to the daytime sleepiness and fatigue associated with sleep disturbance. Sleep apnea affects not only adults but some children as well.

Symptoms of sleep apnea include excessive daytime sleepiness (EDS) and impaired alertness. In other words, common effects of sleep apnea include daytime fatigue, a slower reaction time, and vision problems. OSA may increase risk for driving accidents and work-related accidents. If OSA is not treated, one has an increased risk of other health problems such as diabetes. Even death could occur from untreated OSA due to lack of oxygen to the body. Moreover, people with sleep apnea are examined using "standard test batteries" in order to further identify parts of the brain that may be adversely affected by sleep apnea, including those that govern: "executive functioning", the way the person plans and initiates tasks; attention, working effectively and processing information when in a waking state; using memory and learning. Due to the disruption in daytime cognitive state, behavioral effects are also present. These include moodiness, belligerence, as well as a decrease in attentiveness and drive. Another symptom of sleep apnea is waking up in sleep paralysis. In severe cases, the fear of sleep due to sleep paralysis can lead to insomnia. These effects become very hard to deal with, thus the development of depression may transpire.

There is some evidence that the risk of diabetes among those with moderate or severe sleep apnea is higher. There is also increasing evidence that sleep apnea may also lead to liver function impairment, particularly fatty liver diseases.

Sleep apnea can affect people regardless of sex, race, or age. Risk factors include being male, overweight, obese, or over the age of 40; or having a large neck size (greater than 16-17 inches), enlarged tonsils, enlarged tongue, small jaw bone, gastroesophageal reflux, allergies, sinus problems, family history of sleep apnea, or deviated septum causing nasal obstruction. Alcohol, sedatives and tranquilizers also promote sleep apnea by relaxing the throat. People who smoke have sleep apnea at three times the rate of people who have never smoked. All the factors above may contribute to obstructive sleep apnea. Central sleep apnea is more influenced by being male, being older than 65 years, having heart disorders such as atrial fibrillation, and stroke or brain tumor. Brain tumors may hinder the brain's ability to regulate normal breathing. High blood pressure is also very common in people with sleep apnea.

In adults, the most common cause of OSA is excess weight and obesity, which is associated with soft tissue of the mouth and throat. During sleep, when throat and tongue muscles are more relaxed, this soft tissue can cause the airway to become blocked. In children, causes of OSA often include enlarged tonsils or adenoids, and dental conditions such as a large overbite. Less common causes include a tumor or growth in the airway, and birth defects such as Down syndrome and Pierre-Robin syndrome. Although childhood obesity may cause OSA, it is much less commonly associated with the condition than adult obesity.

For many patients with sleep disorders, including sleep apena, the first and best treatment is weight loss. Although not everyone with sleep apnea is overweight, but most patients are and it is theorized that losing weight helps eliminate fat that blocks the windpipe, resulting in the sleep apnea.

Caloric restriction (CR) increases lifespan and slows age-related degenerative changes in many species, including yeast, worms, flies, rodents, monkeys and perhaps humans. Caloric restriction influences certain signaling pathways that regulate key cell functions, including the insulin/insulin-like growth factor-1 pathway, the nutrient-responsive 'target of rapamycin (TOR)' pathway, and also the activity of protein deacetylase enzymes. Certain protein deacetylases regulate the DNA-binding activity of histone proteins, which in turn, regulates the transcription and expression of specific genes, thus affecting cell and organ functions.

Caloric restriction, like fasting, triggers utilization of stored fat reserves as an energy source. Fat oxidation leads to elevated circulating levels of ketone bodies—small metabolites, such as acetoacetate and beta-hydroxybutyrate (BOHB)—which are used as an alternative energy source by some tissues, such as the brain, when glucose levels are low (NEWMAN, J. C., et al., Ketone bodies as signaling metabolites, *Trends Endocrinology and Metabolism*, 2014, pp 42 Vol 25, Issue 1).

Recently published data indicates that BOHB is not simply an alternative metabolic fuel, but unexpectedly also has specific cell signaling and regulatory actions; actions that may mediate certain of the longevity-promoting effects associated with caloric restriction. In particular, BOHB has been shown to directly inhibit certain histone deacetylase enzymes (HDACs), and BOHB treatment of cultured cells increases histone acetylation, similar that observed with fasting in animals (SHIMAZU, T. et al. Suppression of Oxidative Stress by Beta-Hydroxybutyrate, an Endogenous Histone Deacetylase Inhibitor, *Science*, 2013, pp 211 Vol. 339). BOHB treatment of mice increases histone acetylation and thereby alters expression of certain genes associated with resistance to oxidative stress, notably the FOXO3 gene, a mammalian version of the transcription factor DAF16 that is a key regulator of lifespan in worms. HDAC inhibition by BOHB may also regulate the acetylation state and activity of non-histone proteins that also have cell protective effects.

Recently, BOHB was reported to inhibit the NLRP3 inflammasome, a sensor of the innate immune system which normally triggers inflammatory responses to a variety of injurious agents, such as excess glucose, urate, and amyloids that are associated with some chronic diseases. The known anti-inflammatory effects of fasting or ketogenic diets have been attributed to this effect of BOHB (YOUM, Y. H., et al., The ketone metabolite beta-hydroxybutyrate blocks NLRP3 inflammasome-mediated inflammatory disease, *Nature Medicine*, 2015, pp 263, Vol. 21, Issue 3).

Published data also indicates that BOHB binds to two specific cell-surface receptors (GPR109 and GPR41; TAGGART, A. K., et al., D-Beta-Hydroxybutyrate inhibits adipocyte lipolysis via the nicotinic acid receptor PUMB-G, *J. Biol. Chem.*, 2005, pp 26649, Vol. 280; and KIMURA, I., et al. Short-chain fatty acids and ketones directly regulate sympathetic nervous system via GPR41, *Proc. Natl. Acad. Sci. USA*, 2011, pp 8030, Vol. 108). BOHB binding to GPR41, a G-protein coupled receptor expressed in sympathetic neurons, suppresses sympathetic activity, reduces fat oxidation, and reduces overall metabolic rate in mice. In the worm (*C. elegans*), BOHB treatment is reported to increase lifespan by ~20% (EDWARDS, C., et al., D-Beta-Hydroxybutyrate extends lifespan in *C. elegans, Aging,* 2014, pp 621, Vol. 6, Issue 8).

Fasting is not the only means to elevate ketone body levels. Ketogenic diets—which reduce carbohydrate intake—also increase circulating BOHB levels. Ketogenic diets in animals elicit many of the biochemical changes associated with cellular protection from oxidative stress and with increased lifespan.

Canagliflozin treatment of diabetic patients, by inhibiting renal SGLT2 activity, induces glucosuria, which leads to increased utilization of stored fat reserves (resulting in reduced adiposity and body weight loss). Like fasting and ketogenic diets, canagliflozin treatment of diabetic patients also induces an increase in circulating ketone body levels, including BOHB.

There remains a need to provide an effective treatment for obesity and obesity related disorders (including disorders, diseases and conditions that are a result of, that are exacerbated by and/or that are hastened by obesity).

SUMMARY OF THE INVENTION

The present invention is directed to methods for treating, delaying, slowing the progression of and/or preventing obesity and obesity related disorders comprising administering to a subject in need thereof, a therapeutically effective amount of co-therapy comprising (a) canagliflozin; wherein the canagliflozin is administered in an amount in the range of from about 50 mg to about 500 mg per day (preferably in an amount in the range of from about 100 mg to about 300 mg, more preferably in an amount of about 100 mg or an amount of about 300 mg); and (b) phentermine; wherein the phentermine is administered in an amount in the range of from about 3.75 mg to about 50 mg per day (preferably in an amount in the range of from about 3.75 to about 37.5 mg, more preferably in an amount of about 3.75 mg, about 7.5 mg, about 15 mg, about 30 mg, or about 37.5 mg).

The present invention is directed to a method for treating obesity, for promoting weight loss and/or for suppressing appetite comprising administering to a subject in need thereof a therapeutically effective amount of co-therapy comprising:

(a) canagliflozin; wherein the canagliflozin is administered in an amount in the range of from about 50 mg to about 500 mg per day (preferably in an amount in the range of from about 100 mg to about 300 mg, more preferably in an amount of about 100 mg or an amount of about 300 mg); and (b) phentermine; wherein the phentermine is administered in an amount in the range of from about 3.75 mg to about 50 mg per day (preferably in an amount in the range of from about 3.75 to about 37.5 mg, more preferably in an amount of about 3.75 mg, about 7.5 mg, about 15 mg, about 30 mg, or about 37.5 mg).

The present invention is directed to a method for decreasing food intake, inducing satiety or controlling weight gain, comprising administering to a subject in need thereof a therapeutically effective amount of co-therapy comprising:

(a) canagliflozin; wherein the canagliflozin is administered in an amount in the range of from about 50 mg to about 500 mg per day (preferably in an amount in the range of from about 100 mg to about 300 mg, more preferably in an amount of about 100 mg or an amount of about 300 mg); and (b) phentermine; wherein the phentermine is administered in an amount in the range of from about 3.75 mg to about 50 mg per day (preferably in an amount in the range of from about 3.75 to about 37.5 mg, more preferably in an amount of about 3.75 mg, about 7.5 mg, about 15 mg, about 30 mg, or about 37.5 mg).

In certain embodiments, the present invention is directed to a method for chronic weight management, comprising administering to a subject in need thereof a therapeutically effective amount of co-therapy comprising:

(a) canagliflozin; wherein the canagliflozin is administered in an amount in the range of from about 50 mg to about 500 mg per day (preferably in an amount in the range of from about 100 mg to about 300 mg, more preferably in an amount of about 100 mg or an amount of about 300 mg); and (b) phentermine; wherein the phentermine is administered in an amount in the range of from about 3.75 mg to about 50 mg per day (preferably in an amount in the range of from about 3.75 to about 37.5 mg, more preferably in an amount of about 3.75 mg, about 7.5 mg, about 15 mg, about 30 mg, or about 37.5 mg).

In certain embodiments, the present invention is directed to methods for treating obesity, for promoting weight loss, for suppressing appetite, for decreasing food intake, for inducing satiety and/or for controlling weight gain, comprising identifying a subject in need thereof by determining the body mass index (BMI) of said subject; and wherein the body mass index of said subject is greater than or equal to about 25 kg/m$^2$ (preferably greater than or equal to about 30 kg/m$^2$), administering a therapeutically effective amount of co-therapy comprising (a) canagliflozin; wherein the canagliflozin is administered in an amount in the range of from about 50 mg to about 500 mg per day (preferably in an amount in the range of from about 100 mg to about 300 mg, more preferably in an amount of about 100 mg or an amount of about 300 mg); and (b) phentermine; wherein the phentermine is administered in an amount in the range of from about 3.75 mg to about 50 mg per day (preferably in an amount in the range of from about 3.75 to about 37.5 mg, more preferably in an amount of about 3.75 mg, about 7.5 mg, about 15 mg, about 30 mg, or about 37.5 mg).

The present invention is further directed to a method of weight loss, a method of treating obesity, or a method of treating an obesity related disorder, comprising administering to a subject in need thereof a therapeutically effective amount of co-therapy comprising (a) canagliflozin; wherein the canagliflozin is administered in an amount in the range of from about 50 mg to about 500 mg per day (preferably in an amount in the range of from about 100 mg to about 300 mg, more preferably in an amount of about 100 mg or an amount of about 300 mg); and (b) phentermine; wherein the phentermine is administered in an amount in the range of from about 3.75 mg to about 50 mg per day (preferably in an amount in the range of from about 3.75 to about 37.5 mg, more preferably in an amount of about 3.75 mg, about 7.5 mg, about 15 mg, about 30 mg, or about 37.5 mg).

and wherein the amount of weight loss achieved after 26 weeks is about 5%, preferably about 7.5%, more preferably.

In an embodiment, the present invention is directed to a method of weight loss, a method of treating obesity, or a method of treating an obesity related disorder comprising administering to a subject in need thereof a therapeutically effective amount of co-therapy comprising canagliflozin and phentermine, as described herein, wherein the subject achieves or experiences a weight loss in the range of from about 5% to about 10%, or any amount or range therein, preferably a weight loss of at least about 5%, more preferably, a weight loss of at least about 7.5%, within about 26 Weeks.

In another embodiment, the present invention is directed to a method of weight loss, a method of treating obesity, or a method of treating an obesity related disorder comprising administering to a subject in need thereof a therapeutically effective amount of co-therapy comprising canagliflozin and phentermine, as described herein, wherein the subject achieves or experiences a weight loss in the range of from about 5% to about 10%, or any amount or range therein, preferably a weight loss of at least about 5%, more preferably, a weight loss of at least about 7.5%, within a time period of between about 26 weeks and about 104 weeks, preferably within a time period of about 26 weeks and about 52 weeks.

In another embodiment, the present invention is directed to a method of weight loss, a method of treating obesity, or a method of treating an obesity related disorder comprising administering to a subject in need thereof a therapeutically effective amount of co-therapy comprising canagliflozin and phentermine, as described herein, wherein the co-therapy is administered in conjunction with diet and exercise counseling. In another embodiment, the present invention is directed to a method of weight loss, a method of treating obesity, or a method of treating an obesity related disorder comprising administering to a subject in need thereof co-therapy comprising canagliflozin and phentermine, as described herein, wherein the co-therapy is administered in conjunction with a diet and exercise program. In certain embodiments of the present invention, diet and exercise counseling or diet and exercise program comprises (a) advising the subject to increase physical activity, (b) advising the subject to reduce dietary fat content and/or (c) advising the subject to consume fewer calories. In certain embodiments, the present invention is directed to a method for chronic weight management comprising administering to a subject in need thereof co-therapy comprising canagliflozin and phentermine, as described herein, preferably wherein the co-therapy is an adjunct to a reduced-calorie diet and increased physical activity.

In certain embodiments of the present invention, a subject in need thereof is a subject (an adult or child) whose determined (e.g. measured) body mass index (BMI) is greater than or equal to about 23 kg/m$^2$. In certain additional embodiments of the present invention, a subject in need thereof is a subject (an adult or child) whose determined (e.g. measured) body mass index is greater than or equal to about 25 kg/m$^2$. In certain additional embodiments of the present invention, a subject in need thereof is a subject (an adult or child) whose determined (e.g. measured) body mass index is greater than or equal to about 30 kg/m$^2$. In certain additional embodiments of the present invention, a subject in need thereof is a subject (an adult or child) whose determined (e.g. measured) body mass index is greater than or equal to about 35 kg/m$^2$. In certain additional embodiments of the present invention, a subject in need thereof is a subject (an adult or child) whose determined (e.g. measured) body mass index is in the range of from about 23 kg/m$^2$ to about 29.9 kg/m$^2$.

In certain embodiments of the present invention, a subject in need thereof is a subject (an adult or child) whose determined (e.g. measured) body mass index is greater than or equal to about 23 kg/m$^2$, preferably greater than or equal to about 25 kg/m$^2$, more preferably greater than or equal to about 30 kg/m$^2$, more preferably greater than or equal to about 40 kg/m$^2$ and which subject is diagnosed with or exhibits at least one symptom of a co-morbid condition selected from the group consisting of pre-diabetes, impaired oral glucose tolerance, Type II diabetes mellitus, Metabolic syndrome (also known as Syndrome X), cardiovascular risk factors, a renal or fatty liver disorder (including but not limited to NASH, NAFLD, and the like), sleep apnea, and the like. In another embodiment, the co-morbid condition is selected from the group consisting of pre-diabetes, impaired oral glucose tolerance, Type II diabetes mellitus and Metabolic Syndrome (also known as Syndrome X). In another embodiment, the co-morbid condition is selected from the group consisting cardiovascular risk factors and a renal or fatty liver disorder (including but not limited to NASH, NAFLD, and the like).

In certain embodiments of the present invention, a subject in need thereof is a subject with an initial body mass index greater than or equal to about 30 kg/m$^2$; or greater than or equal to about 27 kg/m$^2$ and diagnosed with or exhibits at least one weight-related co-morbid condition (such as, e.g., hypertension, dyslipidemia, pre-diabetes, or Type II diabetes mellitus).

In certain embodiments of the present invention, a subject in need thereof is a subject whose waist-to-hip ratio is greater than or equal to 1.0 if the subject is a male or is greater than or equal to about 0.8 if the subject is a female. In certain additional embodiments of the present invention, a subject in need thereof is a subject whose waist circumference is >40 inches or 102 cm if the subject is a male or is >35 inches or 94 cm if the subject is a female.

In certain embodiments of the present invention, a subject in need thereof is a subject whose body fat content is greater than about 25%, preferably greater than about 30%. In certain additional embodiments, a subject in need thereof is a subject whose body fat content is greater than about 25% is the subject is a male or greater than about 30% if the subject is female.

In certain embodiments, the present invention is directed to methods for treating obesity, promoting weight loss, suppressing appetite, decreasing food intake, inducing satiety and/or controlling weight gain, in a subject in need thereof, wherein the subject in need thereof is a candidate for or has had bariatric surgery (including gastric bypass surgery, gastric/stomach band surgery, and the like).

In certain embodiments, the present invention is directed to methods for treating obesity, promoting weight loss, suppressing appetite, decreasing food intake, inducing satiety and/or controlling weight gain, in a subject in need thereof, wherein the subject in need thereof is a candidate for or has had implanted a weight loss promoting medical device (for example, an endoluminal sleeve, an intragastric balloon, a device that reduces or reallocates the volume of a subject's gastrointestinal lumen, a device which delivers an electrical current to stimulate the stomach or other nerves of the digestive tract, a device which delivers electrical charges to inhibit the vagus nerve leading to the stomach, a deep-brain stimulation device, a device that delivers an electrical charge to parts of the nervous system that are activated by exercise, and the like).

In an embodiment, the present invention is directed to a method of treating obesity comprising administering to a subject in need thereof a therapeutically effective amount of any the co-therapy as herein described. In another embodiment, the present invention is directed to a method of promoting weight loss comprising administering to a subject in need thereof a therapeutically effective amount of the co-therapy as herein described. In another embodiment, the present invention is directed to a method of suppressing appetite comprising administering to a subject in need thereof a therapeutically effective amount of the co-therapy as herein described. In another embodiment, the present invention is directed to a method of decreasing food intake comprising administering to a subject in need thereof a therapeutically effective amount of the co-therapy as herein described. In another embodiment, the present invention is directed to a method of inducing satiety comprising administering to a subject in need thereof a therapeutically effective amount of the co-therapy as herein described. In another embodiment, the present invention is directed to a method of controlling weight gain comprising administering to a subject in need thereof a therapeutically effective amount of the co-therapy as herein described.

In an embodiment, the present invention is directed to methods for treating obesity, for promoting weight loss, for suppressing appetite, for decreasing food intake, for inducing satiety and/or for controlling weight gain, wherein the subject in need thereof has a measure BMI of greater than about 25 kg/m$^2$ and who has one or more concomitant (or co-existing) conditions selected from the group consisting of pre-diabetes, impaired oral glucose tolerance, Type II diabetes mellitus, Metabolic syndrome (also known as Syndrome X), cardiovascular risk factors, a renal or fatty liver disorder (including but not limited to NASH, NAFLD, and the like) and sleep apnea.

In another embodiment, the present invention is directed to methods for treating of obesity, promoting weight loss, suppressing appetite, decreasing food intake, inducing satiety and/or controlling weight loss wherein the subject in need thereof has a measure BMI of greater than about 25 kg/m$^2$ and who has one or more concomitant (or co-existing) conditions selected from the group consisting of pre-diabetes, impaired oral glucose tolerance, Type II diabetes mellitus and Metabolic syndrome (also known as Syndrome X). In another embodiment, the present invention is directed to methods for treating of obesity, promoting weight loss, suppressing appetite, decreasing food intake, inducing satiety and/or controlling weight loss wherein the subject in need thereof has a measure BMI of greater than about 25 kg/m$^2$ and who has one or more concomitant (or co-existing) conditions selected from the group consisting cardiovascular risk factors and a renal or fatty liver disorder (including but not limited to NASH, NAFLD, and the like).

The present invention is further directed to methods for treating, delaying, slowing the progression and/or preventing a metabolic disorder (including, but not limited to hyperglycemia, pre-diabetes, impaired oral glucose tolerance, impaired fasting blood glucose, postprandial hyperglycemia, hyperinsulinemia, insulin resistance, Type 2 diabetes mellitus (including, but not limited to late stage Type 2 diabetes mellitus), Type 1 diabetes, MODY, LADA, NODAT, gestational diabetes, insufficient glycemic control (or inadequate glycemic control) and Metabolic Syndrome (also known as Syndrome X)), comprising administering to a subject in need thereof a therapeutically effective amount of co-therapy comprising (a) canagliflozin; wherein the canagliflozin is administered in an amount in the range of from about 50 mg to about 500 mg per day (preferably in an amount in the range of from about 100 mg to about 300 mg, more preferably in an amount of about 100 mg or an amount of about 300 mg); and (b) phentermine; wherein the phentermine is administered in an amount in the range of from about 3.75 mg to about 50 mg per day (preferably in an amount in the range of from about 3.75 to about 37.5 mg, more preferably in an amount of about 3.75 mg, about 7.5 mg, about 15 mg, about 30 mg, or about 37.5 mg).

In an embodiment of the present invention, the metabolic disorder is selected from the group consisting of pre-diabetes, impaired oral glucose tolerance, impaired fasting blood glucose, insulin resistance, Type 2 diabetes mellitus and Syndrome X. In another embodiment of the present invention, the metabolic disorder is selected from the group consisting of Type 1 diabetes mellitus, Type 2 diabetes mellitus, maturity onset diabetes of the youth (MODY), latent autoimmune diabetes of adults (LADA) and pre-diabetes.

In an embodiment of the present invention, the subject in need thereof has been diagnosed with or shows symptoms of one or more of the following conditions Type 1 diabetes mellitus, Type 2 diabetes mellitus, maturity onset diabetes of the youth (MODY), latent autoimmune diabetes of adults (LADA) or pre-diabetes. In another embodiment of the present invention, the subject in need thereof has been diagnosed with or shows symptoms of Type 2 diabetes mellitus and/or diabetic nephropathy. In another embodiment of the present invention, the subject in need thereof has been diagnosed with or shows symptoms of Type 2 diabetes mellitus and/or insufficient glycemic control.

In another embodiment of the present invention, the subject in need thereof is:
(1) an individual diagnosed of one or more of the conditions selected from the group consisting of overweight, obesity, visceral obesity and abdominal obesity; or
(2) an individual who shows one, two or more of the following signs:
  (a) a fasting blood glucose or serum glucose concentration greater than about 100 mg/dL, in particular greater than about 125 mg/dL;
  (b) a postprandial plasma glucose equal to or greater than about 140 mg/dL;
  (c) an HbA1c value equal to or greater than about 7.0%;
(3) an individual wherein one, two, three or more of the following conditions are present:
  (a) obesity, visceral obesity and/or abdominal obesity,
  (b) triglyceride blood level equal to or greater than about 150 mg/dL,
  (c) HDL-cholesterol blood level less than about 40 mg/dL in female patients and less than about 50 mg/dL in male patients,
  (d) a systolic blood pressure equal to or greater than about 130 mm Hg and a diastolic blood pressure equal to or greater than about 85 mm Hg,
  (e) a fasting blood glucose level equal to or greater than about 100 mg/dL; or
(4) an individual with obesity.

In an embodiment, the present invention is directed to methods for preventing, slowing the development or slowing the progression of Type 2 diabetes mellitus comprising administering to a subject in need thereof a therapeutically effective amount of co-therapy comprising
(a) canagliflozin; wherein the canagliflozin is administered in an amount in the range of from about 50 mg to about 500 mg per day (preferably in an amount in the range of from about 100 mg to about 300 mg, more preferably in an amount of about 100 mg or an amount of about 300 mg); and
(b) phentermine; wherein the phentermine is administered in an amount in the range of from about 3.75 mg to about 50 mg per day (preferably in an amount in the range of from about 3.75 to about 37.5 mg, more preferably in an amount of about 3.75 mg, about 7.5 mg, about 15 mg, about 30 mg, or about 37.5 mg).

The present invention is further directed to methods of providing cardiovascular protection comprising administering to a subject in need thereof a therapeutically effective amount of co-therapy comprising
(a) canagliflozin; wherein the canagliflozin is administered in an amount in the range of from about 50 mg to about 500 mg per day (preferably in an amount in the range of from about 100 mg to about 300 mg, more preferably in an amount of about 100 mg or an amount of about 300 mg); and
(b) phentermine; wherein the phentermine is administered in an amount in the range of from about 3.75 mg to about 50 mg per day (preferably in an amount in the range of from about 3.75 to about 37.5 mg, more preferably in an amount of about 3.75 mg, about 7.5 mg, about 15 mg, about 30 mg, or about 37.5 mg).

The present invention is further directed to methods for preventing a major adverse cardiac event (MACE) (for example, myocardial infarction, unstable angina, cardiovascular death, revascularization, fatal or non-fatal cerebrovascular accident, peripheral arteriopathy, aortic events, hospitalization due to congestive heart failure) comprising administering to a subject in need thereof, a therapeutically effective amount of co-therapy comprising
(a) canagliflozin; wherein the canagliflozin is administered in an amount in the range of from about 50 mg to about 500 mg per day (preferably in an amount in the range of from about 100 mg to about 300 mg, more preferably in an amount of about 100 mg or an amount of about 300 mg); and
(b) phentermine; wherein the phentermine is administered in an amount in the range of from about 3.75 mg to about 50 mg per day (preferably in an amount in the range of from about 3.75 to about 37.5 mg, more preferably in an amount of about 3.75 mg, about 7.5 mg, about 15 mg, about 30 mg, or about 37.5 mg).

The present invention is further directed to methods for treating, delaying, slowing the progression of and/or preventing a cardiovascular event (including major adverse cardiac events (MACE) such as myocardial infarction, unstable angina, cardiovascular death, revascularization, fatal or non-fatal cerebrovascular accident, peripheral arteriopathy, aortic events, hospitalization due to congestive heart failure, and the like); comprising administering to a subject in need thereof a therapeutically effective amount of co-therapy comprising
(a) canagliflozin; wherein the canagliflozin is administered in an amount in the range of from about 50 mg to about 500 mg per day (preferably in an amount in the range of from about 100 mg to about 300 mg, more preferably in an amount of 100 mg or about 300 mg); and
(b) phentermine; wherein the phentermine is administered in an amount in the range of from about 3.75 mg to about 50 mg per day (preferably in an amount in the range of from about 3.75 to about 37.5 mg, more preferably in an amount of about 3.75 mg, about 7.5 mg, about 15 mg, about 30 mg, or about 37.5 mg).

In an embodiment of the present invention the MACE or cardiovascular event is selected from the group consisting of myocardial infarction, unstable angina, cardiovascular death, revascularization, fatal or non-fatal cerebrovascular accident (e.g. stroke), peripheral arteriopathy, aortic event and hospitalization due to congestive heart failure. In another embodiment of the present invention, the cardiovascular event is selected from the group consisting of myocardial infarction, fatal or non-fatal cerebrovascular accident (e.g. stroke) or hospitalization due to congestive heart failure. In another embodiment of the present invention the MACE or cardiovascular event is myocardial infarction or fatal or non-fatal cerebrovascular event (e.g. stroke). In another embodiment of the present invention the MACE or cardiovascular event is fatal or non-fatal cerebrovascular event (e.g. stroke). In another embodiment of the present invention the MACE or cardiovascular event is myocardial infarction.

In an embodiment, the present invention is directed to methods for decreasing blood pressure, preferably decreasing systolic blood pressure, comprising administering to a subject in need thereof a therapeutically effective amount of co-therapy comprising (a) canagliflozin; wherein the canagliflozin is administered in an amount in the range of from about 50 mg to about 500 mg per day (preferably in an amount in the range of from about 100 mg to about 300 mg, more preferably in an amount of about 100 mg or an amount of about 300 mg); and (b) phentermine; wherein the phentermine is administered in an amount in the range of from about 3.75 mg to about 50 mg per day (preferably in an amount in the range of from about 3.75 to about 37.5 mg, more preferably in an amount of about 3.75 mg, about 7.5 mg, about 15 mg, about 30 mg, or about 37.5 mg).

The present invention is further directed to methods for treating, delaying, slowing the progression of and/or preventing a renal or fatty liver disorder (including, but not limited to NASH, NAFLD, and the like) comprising administering to a subject in need thereof a therapeutically effective amount of co-therapy comprising (a) canagliflozin; wherein the canagliflozin is administered in an amount in the range of from about 50 mg to about 500 mg per day (preferably in an amount in the range of from about 100 mg to about 300 mg, more preferably in an amount of about 100 mg or an amount of about 300 mg); and (b) phentermine; wherein the phentermine is administered in an amount in the range of from about 3.75 mg to about 50 mg per day (preferably in an amount in the range of from about 3.75 to about 37.5 mg, more preferably in an amount of about 3.75 mg, about 7.5 mg, about 15 mg, about 30 mg, or about 37.5 mg).

In an embodiment of the present invention, the renal or fatty liver disorder is selected from the group consisting of alcoholic simple fatty liver, alcoholic steatohepatitis (ASH), alcoholic hepatic fibrosis, alcoholic cirrhosis, nonalcoholic fatty liver disease (NAFLD), nonalcoholic simple fatty liver, nonalcoholic steatohapatitis (NASH), nonalcoholic hepatic fibrosis, and nonalcoholic cirrhosis. In another embodiment of the present invention, the renal or fatty liver disorder is selected from the group consisting of nonalcoholic fatty liver disease (NAFLD), nonalcoholic simple fatty liver, nonalcoholic steatohapatitis (NASH), nonalcoholic hepatic fibrosis, and nonalcoholic cirrhosis. In another embodiment of the present invention, the renal or fatty liver disorder is selected from the group consisting of NAFLD and NASH. In another embodiment of the present invention, the renal disorder is diabetic nephropathy.

In another embodiment of the present invention, the renal or fatty liver disorder is selected from the group consisting of hyperfiltrative diabetic nephropathy, renal hyperfiltration, glomerular hyperfiltration, renal allograft hyperfiltration, compensatory hyperfiltration, hyperfiltrative chronic kidney disease and hyperfiltrative acute renal failure. In another embodiment of the present invention, the renal disorder is selected from the group consisting of microalbuminuria, macroalbuminuria, elevated urine albumin levels and elevated albumin/creatinine ratio (ACR).

The present invention is further directed to methods for (a) treating, delaying, slowing the progression of, inducing remission of or preventing microalbuminuria (elevated urine albumin levels); (b) treating, delaying, slowing the progression of, or preventing macroalbuminuria; (c) decreasing urine albumin levels; and/or (d) decreasing albumin/creatinine ratio (ACR); comprising administering to subject in need thereof a therapeutically effective amount of co-therapy comprising (a) canagliflozin; wherein the canagliflozin is administered in an amount in the range of from about 50 mg to about 500 mg per day (preferably in an amount in the range of from about 100 mg to about 300 mg, more preferably in an amount of about 100 mg or an amount of about 300 mg); and (b) phentermine; wherein the phentermine is administered in an amount in the range of from about 3.75 mg to about 50 mg per day (preferably in an amount in the range of from about 3.75 to about 37.5 mg, more preferably in an amount of about 3.75 mg, about 7.5 mg, about 15 mg, about 30 mg, or about 37.5 mg).

The present invention is further directed to methods for preventing, slowing the progression of, delaying and/or treating renal hyperfiltrative injury comprising administering to a subject in need thereof a therapeutically effective amount of co-therapy comprising (a) canagliflozin; wherein the canagliflozin is administered in an amount in the range of from about 50 mg to about 500 mg per day (preferably in an amount in the range of from about 100 mg to about 300 mg, more preferably in an amount of about 100 mg or an amount of about 300 mg); and (b) phentermine; wherein the phentermine is administered in an amount in the range of from about 3.75 mg to about 50 mg per day (preferably in an amount in the range of from about 3.75 to about 37.5 mg, more preferably in an amount of about 3.75 mg, about 7.5 mg, about 15 mg, about 30 mg, or about 37.5 mg).

The present invention is further directed to methods for preventing, slowing the progression of, delaying or treating a condition or disorder selected from the group consisting of hyperfiltrative diabetic nephropathy, renal hyperfiltration, glomerular hyperfiltration, renal allograft hyperfiltration, compensatory hyperfiltration (e.g. after renal mass reduction by surgery), hyperfiltrative chronic kidney disease, hyperfiltrative acute renal failure, and obesity comprising administering to a subject in need thereof, co-therapy comprising (a) canagliflozin; wherein the canagliflozin is administered in an amount in the range of from about 50 mg to about 500 mg per day (preferably in an amount in the range of from about 100 mg to about 300 mg, more preferably in an amount of about 100 mg or an amount of about 300 mg); and (b) phentermine; wherein the phentermine is administered in an amount in the range of from about 3.75 mg to about 50 mg per day (preferably in an amount in the range of from about 3.75 to about 37.5 mg, more preferably in an amount of about 3.75 mg, about 7.5 mg, about 15 mg, about 30 mg, or about 37.5 mg).

The present invention is further directed to methods for treating, delaying, slowing the progression of and/or preventing diabetic neuropathy comprising administering to a subject in need thereof a therapeutically effective amount of co-therapy comprising (a) canagliflozin; wherein the canagliflozin is administered in an amount in the range of from about 50 mg to about 500 mg per day (preferably in an amount in the range of from about 100 mg to about 300 mg, more preferably in an amount of about 100 mg or an amount of about 300 mg); and (b) phentermine; wherein the phentermine is administered in an amount in the range of from about 3.75 mg to about 50 mg per day (preferably in an amount in the range of from about 3.75 to about 37.5 mg, more preferably in an amount of about 3.75 mg, about 7.5 mg, about 15 mg, about 30 mg, or about 37.5 mg).

In an embodiment of the present invention, the subject in need thereof has been diagnosed with or shows symptoms of one or more of the following conditions:
(a) diabetes mellitus, regardless of type;
(b) chronic kidney disease (CKD);
(c) acute renal failure (ARF);
(d) renal transplant recipients;
(e) renal transplant donors; or
(f) unilateral total or partial nephrectomized patients; or
(g) nephrotic syndrome.

The present invention is further directed to methods for treating or preventing a sleep disorder (including, but not limited to sleep apnea, and the like) comprising administering to a subject in need thereof a therapeutically effective amount of co-therapy comprising (a) canagliflozin; wherein the canagliflozin is administered in an amount in the range of from about 50 mg to about 500 mg per day (preferably in an amount in the range of from about 100 mg to about 300 mg, more preferably in an amount of about 100 mg or an amount of about 300 mg); and (b) phentermine; wherein the phentermine is administered in an amount in the range of from about 3.75 mg to about 50 mg per day (preferably in an amount in the range of from about 3.75 to about 37.5 mg, more preferably in an amount of about 3.75 mg, about 7.5 mg, about 15 mg, about 30 mg, or about 37.5 mg).

The present invention is further directed to methods for prolonging the life or life span of a subject, comprising administering to the subject co-therapy comprising (a) canagliflozin; wherein the canagliflozin is administered in an amount in the range of from about 50 mg to about 500 mg per day (preferably in an amount in the range of from about 100 mg to about 300 mg, more preferably in an amount of about 100 mg or an amount of about 300 mg); and (b) phentermine; wherein the phentermine is administered in an amount in the range of from about 3.75 mg to about 50 mg per day (preferably in an amount in the range of from about 3.75 to about 37.5 mg, more preferably in an amount of about 3.75 mg, about 7.5 mg, about 15 mg, about 30 mg, or about 37.5 mg).

The present invention is further directed to methods for treating obesity, for promoting weight loss, for suppressing appetite, for decreasing food intake, for inducing satiety and/or for controlling weight gain, comprising administering to a subject in need thereof a therapeutically effective amount of co-therapy comprising (a) canagliflozin; wherein the canagliflozin is administered in an amount in the range of from about 50 mg to about 500 mg per day (preferably in an amount in the range of from about 100 mg to about 300 mg, more preferably in an amount of about 100 mg or an amount of about 300 mg); and (b) phentermine; wherein the phentermine is administered in an amount in the range of from about 3.75 mg to about 50 mg per day (preferably in an amount in the range of from about 3.75 to about 37.5 mg, more preferably in an amount of about 3.75 mg, about 7.5 mg, about 15 mg, about 30 mg, or about 37.5 mg).

wherein the subject in need thereof is a subject who is taking one or more pharmaceutical agents (drugs) whose potential side effect(s) include weight gain.

The present invention is further directed to methods of treating, delaying, slowing the progression of and/or preventing a disorder selected from the group consisting of shortness of breath, gallbladder disease, cancer (e.g. endometrial, breast, prostate, colon), osteoarthritis, orthopedic problems, reflux esophagitis (heartburn), snoring, polycystic ovary syndrome, stress incontinence, menstrual irregularities, infertility, heart trouble, depression, anxiety, gout, beta-cell dysfunction, hypopnea, comprising administering to a subject in need thereof a therapeutically effective amount of co-therapy comprising (a) canagliflozin; wherein the canagliflozin is administered in an amount in the range of from about 50 mg to about 500 mg per day (preferably in an amount in the range of from about 100 mg to about 300 mg, more preferably in an amount of about 100 mg or an amount of about 300 mg); and (b) phentermine; wherein the phentermine is administered in an amount in the range of from about 3.75 mg to about 50 mg per day (preferably in an amount in the range of from about 3.75 to about 37.5 mg, more preferably in an amount of about 3.75 mg, about 7.5 mg, about 15 mg, about 30 mg, or about 37.5 mg).

In an embodiment, the present invention is directed to methods of treating, delaying, slowing the progression of or preventing obesity and obesity related disorders comprising administering to a subject in need thereof a therapeutically effective amount of co-therapy comprising (a) canagliflozin; wherein the canagliflozin is administered in an amount of about 100 mg per day; and (b) phentermine; wherein the phentermine is administered in an amount of about 3.75 mg per day.

In an embodiment, the present invention is directed to methods of treating, delaying, slowing the progression of or preventing obesity and obesity related disorders comprising administering to a subject in need thereof a therapeutically effective amount of co-therapy comprising (a) canagliflozin; wherein the canagliflozin is administered in an amount of about 100 mg per day; and (b) phentermine; wherein the phentermine is administered in an amount of about 7.5 mg per day.

In an embodiment, the present invention is directed to methods of treating, delaying, slowing the progression of or preventing obesity and obesity related disorders comprising administering to a subject in need thereof a therapeutically effective amount of co-therapy comprising (a) canagliflozin; wherein the canagliflozin is administered in an amount of about 100 mg per day; and (b) phentermine; wherein the phentermine is administered in an amount of about 15 mg per day.

In an embodiment, the present invention is directed to methods of treating, delaying, slowing the progression of or preventing obesity and obesity related disorders comprising administering to a subject in need thereof a therapeutically effective amount of co-therapy comprising (a) canagliflozin; wherein the canagliflozin is administered in an amount of about 100 mg per day; and (b) phentermine; wherein the phentermine is administered in an amount of about 30 mg per day.

In an embodiment, the present invention is directed to methods of treating, delaying, slowing the progression of or preventing obesity and obesity related disorders comprising administering to a subject in need thereof a therapeutically effective amount of co-therapy comprising (a) canagliflozin; wherein the canagliflozin is administered in an amount of about 100 mg per day; and (b) phentermine; wherein the phentermine is administered in an amount of about 37.5 mg per day.

In an embodiment, the present invention is directed to methods of treating, delaying, slowing the progression of or preventing obesity and obesity related disorders comprising administering to a subject in need thereof a therapeutically effective amount of co-therapy comprising (a) canagliflozin; wherein the canagliflozin is administered in an amount of about 300 mg per day; and (b) phentermine; wherein the phentermine is administered in an amount of about 3.75 mg per day.

In an embodiment, the present invention is directed to methods of treating, delaying, slowing the progression of or preventing obesity and obesity related disorders comprising administering to a subject in need thereof a therapeutically effective amount of co-therapy comprising (a) canagliflozin; wherein the canagliflozin is administered in an amount of about 300 mg per day; and (b) phentermine; wherein the phentermine is administered in an amount of about 7.5 mg per day.

In an embodiment, the present invention is directed to methods of treating, delaying, slowing the progression of or preventing obesity and obesity related disorders comprising administering to a subject in need thereof a therapeutically effective amount of co-therapy comprising (a) canagliflozin; wherein the canagliflozin is administered in an amount of about 300 mg per day; and (b) phentermine; wherein the phentermine is administered in an amount of about 15 mg per day.

In an embodiment, the present invention is directed to methods of treating, delaying, slowing the progression of or preventing obesity and obesity related disorders comprising administering to a subject in need thereof a therapeutically effective amount of co-therapy comprising (a) canagliflozin; wherein the canagliflozin is administered in an amount of about 300 mg per day; and (b) phentermine; wherein the phentermine is administered in an amount of about 30 mg per day.

In an embodiment, the present invention is directed to methods of treating, delaying, slowing the progression of or preventing obesity and obesity related disorders comprising administering to a subject in need thereof a therapeutically effective amount of co-therapy comprising (a) canagliflozin; wherein the canagliflozin is administered in an amount of about 300 mg per day; and (b) phentermine; wherein the phentermine is administered in an amount of about 37.5 mg per day.

In another embodiment, the present invention is directed to methods of treating, delaying, slowing the progression of or preventing obesity and obesity related disorders comprising administering to a subject in need thereof a therapeutically effective amount of co-therapy comprising (a) canagliflozin; wherein the canagliflozin is a crystalline hemihydrate; and wherein the canagliflozin is administered in an amount of about 100 mg per day; and (b) phentermine; wherein the phentermine is phentermine hydrochloride and wherein the phentermine is administered in an amount of about 3.75 mg per day.

In another embodiment, the present invention is directed to methods of treating, delaying, slowing the progression of or preventing obesity and obesity related disorders comprising administering to a subject in need thereof a therapeutically effective amount of co-therapy comprising (a) canagliflozin; wherein the canagliflozin is a crystalline hemihydrate; and wherein the canagliflozin is administered in an amount of about 100 mg per day; and (b) phentermine; wherein the phentermine is phentermine hydrochloride and wherein the phentermine is administered in an amount of about 7.5 mg per day.

In another embodiment, the present invention is directed to methods of treating, delaying, slowing the progression of or preventing obesity and obesity related disorders comprising administering to a subject in need thereof a therapeutically effective amount of co-therapy comprising (a) canagliflozin; wherein the canagliflozin is a crystalline hemihydrate; and wherein the canagliflozin is administered in an amount of about 100 mg per day; and (b) phentermine; wherein the phentermine is phentermine hydrochloride and wherein the phentermine is administered in an amount of about 15 mg per day.

In another embodiment, the present invention is directed to methods of treating, delaying, slowing the progression of or preventing obesity and obesity related disorders comprising administering to a subject in need thereof a therapeutically effective amount of co-therapy comprising (a) canagliflozin; wherein the canagliflozin is a crystalline hemihydrate; and wherein the canagliflozin is administered in an amount of about 100 mg per day; and (b) phentermine; wherein the phentermine is phentermine hydrochloride and wherein the phentermine is administered in an amount of about 30 mg per day.

In another embodiment, the present invention is directed to methods of treating, delaying, slowing the progression of or preventing obesity and obesity related disorders comprising administering to a subject in need thereof a therapeutically effective amount of co-therapy comprising (a) canagliflozin; wherein the canagliflozin is a crystalline hemihydrate; and wherein the canagliflozin is administered in an amount of about 100 mg per day; and (b) phentermine; wherein the phentermine is phentermine hydrochloride and wherein the phentermine is administered in an amount of about 37.5 mg per day.

In another embodiment, the present invention is directed to methods of treating, delaying, slowing the progression of or preventing obesity and obesity related disorders comprising administering to a subject in need thereof a therapeutically effective amount of co-therapy comprising (a) canagliflozin; wherein the canagliflozin is a crystalline hemihydrate; and wherein the canagliflozin is administered in an amount of about 300 mg per day; and (b) phentermine; wherein the phentermine is phentermine hydrochloride and wherein the phentermine is administered in an amount of about 3.75 mg per day.

In another embodiment, the present invention is directed to methods of treating, delaying, slowing the progression of or preventing obesity and obesity related disorders comprising administering to a subject in need thereof a therapeutically effective amount of co-therapy comprising (a) canagliflozin; wherein the canagliflozin is a crystalline hemihydrate; and wherein the canagliflozin is administered in an amount of about 300 mg per day; and (b) phentermine; wherein the phentermine is phentermine hydrochloride and wherein the phentermine is administered in an amount of about 7.5 mg per day.

In another embodiment, the present invention is directed to methods of treating, delaying, slowing the progression of or preventing obesity and obesity related disorders comprising administering to a subject in need thereof a therapeutically effective amount of co-therapy comprising (a) canagliflozin; wherein the canagliflozin is a crystalline hemihydrate; and wherein the canagliflozin is administered in an amount of about 300 mg per day; and (b) phentermine;

wherein the phentermine is phentermine hydrochloride and wherein the phentermine is administered in an amount of about 15 mg per day.

In another embodiment, the present invention is directed to methods of treating, delaying, slowing the progression of or preventing obesity and obesity related disorders comprising administering to a subject in need thereof a therapeutically effective amount of co-therapy comprising (a) canagliflozin; wherein the canagliflozin is a crystalline hemihydrate; and wherein the canagliflozin is administered in an amount of about 300 mg per day; and (b) phentermine; wherein the phentermine is phentermine hydrochloride and wherein the phentermine is administered in an amount of about 30 mg per day.

In another embodiment, the present invention is directed to methods of treating, delaying, slowing the progression of or preventing obesity and obesity related disorders comprising administering to a subject in need thereof a therapeutically effective amount of co-therapy comprising (a) canagliflozin; wherein the canagliflozin is a crystalline hemihydrate; and wherein the canagliflozin is administered in an amount of about 300 mg per day; and (b) phentermine; wherein the phentermine is phentermine hydrochloride and wherein the phentermine is administered in an amount of about 37.5 mg per day.

In certain embodiments of the present invention, the canagliflozin is a crystalline, hemihydrate canagliflozin. In certain embodiments of the present invention, the phentermine is phentermine hydrochloride.

In an embodiment of the present invention, canagliflozin is administered in an amount in the range of from about 50 mg to about 500 mg. In another embodiment of the present invention, canagliflozin is administered in an amount in the range of from about 100 mg to about 300 mg. In another embodiment of the present invention, canagliflozin is administered in an amount of about 100 mg. In another embodiment of the present invention, canagliflozin is administered in an amount of about 300 mg.

In an embodiment of the present invention, phentermine is administered in an amount in the range of from about 3.75 mg to about 50 mg. In another embodiment of the present invention, phentermine is administered in an amount in the range of from about 3.75 mg to about 37.5 mg. In another embodiment of the present invention, phentermine is administered in an amount in the range of from about 7.5 mg to about 37.5 mg. In another embodiment of the present invention, phentermine is administered in an amount in the range of from about 7.5 mg to about 15 mg. In another embodiment of the present invention, phentermine is administered in an amount of about 3.75 mg. In another embodiment of the present invention, phentermine is administered in an amount of about 7.5 mg. In another embodiment of the present invention, phentermine is administered in an amount of about 15 mg. In another embodiment of the present invention, phentermine is administered in an amount of about 30 mg. In another embodiment of the present invention, phentermine is administered in an amount of about 37.5 mg.

In another embodiment of the present invention, phentermine is administered in an amount of about 3.75 mg, about 7.5 mg, about 15 mg, about 30 mg or about 37.5 mg. In another embodiment of the present invention, phentermine is administered in an amount of about 3.75 mg, about 7.5 mg or about 15 mg. In another embodiment of the present invention, phentermine is administered in an amount of about 7.5 mg or about 15 mg.

In an embodiment, the co-therapy comprises canagliflozin in an amount of about 100 mg and phentermine in an amount of about 3.75 mg, administered at least once daily (preferably once daily). In another embodiment, the co-therapy comprises canagliflozin in an amount of about 100 mg and phentermine in an amount of about 7.5 mg, administered at least once daily (preferably once daily). In an embodiment, the co-therapy comprises canagliflozin in an amount of about 100 mg and phentermine in an amount of about 15 mg, administered at least once daily (preferably once daily). In an embodiment, the co-therapy comprises canagliflozin in an amount of about 100 mg and phentermine in an amount of about 30 mg, administered at least once daily (preferably once daily). In an embodiment, the co-therapy comprises canagliflozin in an amount of about 100 mg and phentermine in an amount of about 37.5 mg, administered at least once daily (preferably once daily).

In an embodiment, the co-therapy comprises canagliflozin in an amount of about 300 mg and phentermine in an amount of about 3.75 mg, administered at least once daily (preferably once daily). In another embodiment, the co-therapy comprises canagliflozin in an amount of about 300 mg and phentermine in an amount of about 7.5 mg, administered at least once daily (preferably once daily). In an embodiment, the co-therapy comprises canagliflozin in an amount of about 300 mg and phentermine in an amount of about 15 mg, administered at least once daily (preferably once daily). In an embodiment, the co-therapy comprises canagliflozin in an amount of about 300 mg and phentermine in an amount of about 30 mg, administered at least once daily (preferably once daily). In an embodiment, the co-therapy comprises canagliflozin in an amount of about 300 mg and phentermine in an amount of about 37.5 mg, administered at least once daily (preferably once daily).

Illustrative of the invention is a pharmaceutical composition comprising (a) canagliflozin; wherein the canagliflozin is administered in an amount in the range of from about 50 mg to about 500 mg per day (preferably in an amount in the range of from about 50 mg to about 300 mg, more preferably in an amount of about 50 mg, about 100 mg or about 300 mg); (b) phentermine; wherein the phentermine is administered in an amount in the range of from about 3.75 mg to about 50 mg per day (preferably in an amount in the range of from about 3.75 mg to about 37.5 mg, more preferably in an amount of about 3.75 mg, about 7.5 mg, about 15 mg, about 30 mg or about 37.5 mg); and (c) a pharmaceutically acceptable carrier.

An illustration of the invention is a pharmaceutical composition made by mixing (a) canagliflozin; wherein the canagliflozin is administered in an amount in the range of from about 50 mg to about 500 mg per day (preferably in an amount in the range of from about 50 mg to about 300 mg, more preferably in an amount of about 50 mg, about 100 mg, or about 300 mg); (b) phentermine; wherein the phentermine is administered in an amount in the range of from about 3.75 mg to about 50 mg per day (preferably in an amount in the range of from about 3.75 mg to about 37.5 mg, more preferably in an amount of about 37.5 mg, about 7.5 mg, about 15 mg, about 30 mg or about 37.5 mg); and (c) a pharmaceutically acceptable carrier. Illustrating the invention is a process for making a pharmaceutical composition comprising mixing the product prepared according to the process described herein and a pharmaceutically acceptable carrier.

Exemplifying the invention are methods for treating, delaying, slowing the progression of and/or preventing obesity and obesity related disorders comprising administering to a subject in need thereof a therapeutically effective amount of any of the pharmaceutical compositions described herein.

In another embodiment, the present invention is directed to a composition comprising (a) canagliflozin; wherein the canagliflozin is administered in an amount in the range of from about 50 mg to about 500 mg per day (preferably in an amount in the range of from 50 mg to about 300 mg, more preferably in an amount of about 50 mg, about 100 mg or about 300 mg); (b) phentermine; wherein the phentermine is administered in an amount in the range of from about 37.5 mg to about 50 mg per day (preferably in an amount in the range of from about 3.75 mg to about 37.5 mg, more preferably in an amount of about 3.75 mg, about 7.5 mg, about 15 mg, about 30 mg or about 37.5 mg); and (c) a pharmaceutically acceptable carrier; for treating, delaying, slowing the progression of and/or preventing obesity and obesity related disorders.

BRIEF DESCRIPTION OF THE FIGURE

FIG. 1 illustrates the mean placebo-subtracted weight loss (measured at 0-26 Weeks extrapolated to 52 Weeks) for Canagliflozin, Phentermine and Combination Therapy.

DETAILED DESCRIPTION OF THE INVENTION

The present invention is directed to methods for treating, delaying, slowing the progression of and/or preventing obesity and obesity related disorders (including metabolic disorders such as pre-diabetes, Type 2 diabetes mellitus, Syndrome X, and the like, renal or fatty liver disorders such as NASH, NAFLD, and the like, cardiovascular events (or MACE), sleep apnea, etc.) comprising administering to a subject in need thereof a therapeutically effective amount of co-therapy comprising (a) canagliflozin (preferably the crystalline hemihydrate form of canagliflozin); wherein the canagliflozin is administered in an amount in the range of from about 50 mg to about 500 mg per day (preferably in an amount in the range of from about 50 mg to about 300 mg, more preferably in an amount of about 50 mg, about 100 mg or about 300 mg); and (b) phentermine (preferably phentermine hydrochloride); wherein the phentermine is administered in an amount in the range of from about 3.75 mg to about 50 mg per day (preferably in an amount in the range of from about 3.75 to about 37.5 mg, more preferably in an amount of about 3.75 mg, about 7.5 mg, about 15 mg, about 30 mg, or about 37.5 mg).

As used herein, unless otherwise noted, the term "canagliflozin" shall mean a compound of formula (I-X);

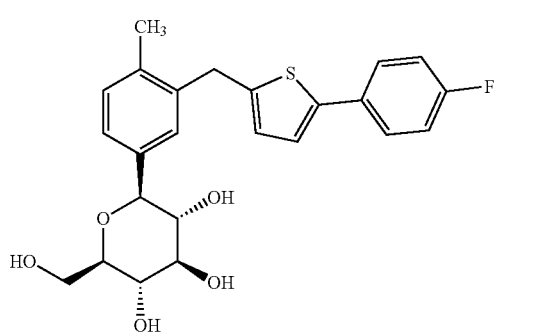

(I-X)

also known as (1S)-1,5-anhydro-1-[3-[[5-(4-fluorophenyl)-2-thienyl]methyl]-4-methylphenyl]-D-glucitol, or a crystalline, hemihydrate form of the compound of formula (I-X). The compound of formula (I-X) exhibits inhibitory activity against sodium-dependent glucose transporter, such as for example SGLT2; and may be prepared according to the process as disclosed in Nomura, S. et al., US Patent Publication, US 2005/0233988 A1, published Oct. 20, 2005, which is incorporated by reference herein.

As used herein, the term "canagliflozin" shall further include a mixture of stereoisomers, or each pure or substantially pure isomer. In addition, the term "canagliflozin" shall include an intramolecular salt, hydrate, solvate or polymorph thereof. In certain embodiments, the term "canagliflozin" shall mean the crystalline hemihydrate form of the compound of formula (I-X), as described in WO 2008/069327, the disclosure of which is hereby incorporated by reference in its entirety.

As used herein, the term "phentermine" shall mean 2-methyl-1-phenylpropan-2-amine and pharmaceutically acceptable salts thereof, preferably phentermine hydrochloride. Phentermine is a sympathomimetic amine anorectic indicated as short-term adjunct in a regimen of weight loss reduction (including exercise, behavioral modification and caloric restriction) in the management of obesity. Phentermine is approved as an appetite suppressant and is medically prescribed as a diet pill; intended for obese patients and patients that are considered a medical risk due to weight. There are various phentermine brands and supplements available through tablets, capsules, and drinks including, VITES, ADIPED, ADIPEX-P, SUPRENZA, IONAMIN and QSYMIA (a co-therapy with topiramate) available in various dosages, including the 15 mg, 30 mg and 37.5 mg.

In certain preferred embodiments, the dosage of phentermine (in mg) shall mean the amount of phentermine free base or free base equivalent (when the phentermine is present as a pharmaceutically acceptable salt thereof, for example as phentermine hydrochloride) that is administered or present in the pharmaceutical composition.

The term "body mass index" or "BMI" of a human patient is defined as the weight in kilograms divided by the square of the height in meters, such that BMI has units of $kg/m^2$. The term "overweight" is defined as the condition wherein the adult individual of Europid origin has a BMI equal to or greater than 25 $kg/m^2$ and less than 30 $kg/m^2$. In subjects of Asian origin the term "overweight" is defined as the condition wherein the adult individual has a BMI equal to or greater than 23 $kg/m^2$ and less than 25 $kg/m^2$. The terms "overweight" and "pre-obese" are used interchangeably.

The term "obesity" is defined as the condition wherein the adult individual of Europid origin has a BMI equal to or greater than 30 $kg/m^2$. According to a WHO definition the term obesity may be categorized as follows: the term "class I obesity" is the condition wherein the BMI is equal to or greater than 30 $kg/m^2$ but lower than 35 $kg/m^2$; the term "class II obesity" is the condition wherein the BMI is equal to or greater than 35 $kg/m^2$ but lower than 40 $kg/m^2$; the terms "class III obesity" is the condition wherein the BMI is equal to or greater than 40 $kg/m^2$. In subjects of Asian origin the term "obesity" is defined as the condition wherein the adult individual has a BMI equal or greater than 25 $kg/m^2$. Obesity in Asians may be categorized further as follows: the term "class I obesity" is the condition wherein the BMI is equal to or greater than 25 $kg/m^2$ but lower than 30 $kg/m^2$; the term "class II obesity" is the condition wherein the BMI is equal to or greater than 30 $kg/m^2$.

The term "visceral obesity" is defined as the condition wherein a waist-to-hip ratio of greater than or equal to 1.0 in men and 0.8 in women is measured. It defines the risk for insulin resistance and the development of pre-diabetes. The term "abdominal obesity" is usually defined as the condition wherein the waist circumference is >40 inches or 102 cm in men, and is >35 inches or 94 cm in women (for normal ranges of populations, see for example "Joint scientific statement (IDF, NHLBI, AHA, WHO, IAS, IASO). Circulation 2009; 120:1640-1645").

The term "morbid obesity" is defined herein as a condition in which the individual of Europid origin has a BMI >40 or has a BMI >35 and a comorbidity such as diabetes mellitus or hypertension (see World Health Organization. Obesity: Preventing and Managing the Global Epidemic: Report on a WHO Consultation. *World Health Organ Tech Rep Ser.* 2000; 894: i-xii, 1-253).

The term "euglycemia" is defined as the condition in which a subject has a fasting blood glucose concentration within the normal range, greater than 70 mg/dL (3.89 mmol/L) and less than 100 mg/dL (5.6 mmol/L), and a 2 h postprandial glucose concentration less than 140 mg/dl.

The term "hyperglycemia" is defined as the condition in which a subject has a fasting blood glucose concentration above the normal range, greater than 100 mg/dL (5.6 mmol/L).

The term "hypoglycemia" is defined as the condition in which a subject has a blood glucose concentration below the normal range, in particular below 70 mg/dL (3.89 mmol/L).

The term "postprandial hyperglycemia" is defined as the condition in which a subject has a 2 hour postprandial blood glucose or serum glucose concentration greater than 200 mg/dL (11.11 mmol/L).

The term "impaired fasting blood glucose" or "IFG" is defined as the condition in which a subject has a fasting blood glucose concentration or fasting serum glucose concentration in a range from 100 to 125 mg/dl (i.e. from 5.6 to 6.9 mmol/l. A subject with "normal fasting glucose" has a fasting glucose concentration smaller than 100 mg/dl, i.e. smaller than 5.6 mmol/l.

The term "impaired glucose tolerance" or "IGT" is defined as the condition in which a subject has a 2 hour postprandial blood glucose or serum glucose concentration greater than 140 mg/dl (7.78 mmol/L) and less than 200 mg/dL (11.11 mmol/L). The abnormal glucose tolerance, i.e. the 2 hour postprandial blood glucose or serum glucose concentration can be measured as the blood sugar level in mg of glucose per dL of plasma 2 hours after taking 75 g of glucose after a fast. A subject with "normal glucose tolerance" has a 2 hour postprandial blood glucose or serum glucose concentration smaller than 140 mg/dl (7.78 mmol/L).

The term "hyperinsulinemia" is defined as the condition in which a subject with insulin resistance, with or without euglycemia, has fasting or postprandial serum or plasma insulin concentration elevated above that of normal, lean individuals without insulin resistance, having a waist-to-hip ratio<1.0 (for men) or <0.8 (for women).

The term "insulin resistance" is defined as a state in which circulating insulin levels in excess of the normal response to a glucose load are required to maintain the euglycemic state (Ford E S, et al. *JAMA*. (2002) 287:356-9). A method of determining insulin resistance is the euglycaemic-hyperinsulinaemic clamp test. The ratio of insulin to glucose is determined within the scope of a combined insulin-glucose infusion technique. There is found to be insulin resistance if the glucose absorption is below the 25th percentile of the background population investigated (WHO definition). Rather less laborious than the clamp test are so called minimal models in which, during an intravenous glucose tolerance test, the insulin and glucose concentrations in the blood are measured at fixed time intervals and from these the insulin resistance is calculated. With this method, it is not possible to distinguish between hepatic and peripheral insulin resistance.

As a rule, other parameters are used in everyday clinical practice to assess insulin resistance. Preferably, the patient's triglyceride concentration is used, for example, as increased triglyceride levels correlate significantly with the presence of insulin resistance.

Patients with a predisposition for the development of IGT or IFG or Type 2 diabetes are those having euglycemia with hyperinsulinemia and are by definition, insulin resistant. A typical patient with insulin resistance is usually overweight or obese. If insulin resistance can be detected, this is a particularly strong indication of the presence of pre-diabetes. Thus, it may be that in order to maintain glucose homoeostasis a person needs 2-3 times as much insulin as a healthy person, without this resulting in any clinical symptoms.

The term "pre-diabetes" is the condition wherein an individual is pre-disposed to the development of type 2 diabetes. Pre-diabetes extends the definition of impaired glucose tolerance to include individuals with a fasting blood glucose within the high normal range 100 mg/dL (J. B. Meigs, et al. Diabetes 2003; 52:1475-1484) and fasting hyperinsulinemia (elevated plasma insulin concentration). The scientific and medical basis for identifying pre-diabetes as a serious health threat is laid out in a Position Statement entitled "The Prevention or Delay of Type 2 Diabetes" issued jointly by the American Diabetes Association and the National Institute of Diabetes and Digestive and Kidney Diseases (Diabetes Care 2002; 25:742-749). Individuals likely to have insulin resistance are those who have two or more of the following attributes: 1) overweight or obese, 2) high blood pressure, 3) hyperlipidemia, 4) one or more $1^{st}$ degree relative with a diagnosis of IGT or IFG or type 2 diabetes.

The term "Type 2 diabetes" is defined as the condition in which a subject has a fasting (i.e., no caloric intake for 8 hours) blood glucose or serum glucose concentration greater than 125 mg/dL (6.94 mmol/L), when measured at minimum two independent occasions. The measurement of blood glucose values is a standard procedure in routine medical analysis. Type 2 diabetes is also defined as the condition in which a subject has HbA1c equal to, or greater than 6.5%, a two hour plasma glucose equal to, or greater than 200 mg/dL (11.1 mmol/L) during an oral glucose tolerance test (OGTT) or a random glucose concentration equal to, or greater than 200 mg/dL (11.1 mmol/L) in conjunction with classic symptoms of hyperglycaemia or hyperglycaemic crisis. In the absence of unequicoval hyperglycaemia, as with most diagnostic tests, a test result diagnostic of diabetes should be repeated to rule out laboratory error. The assessment of HbA1c should be performed using a method certified by the National Glycohemoglobin Standardization Program (NGSP) and standardized or traceable to the Diabetes Control and Complications Trial (DCCT) reference assay. If a OGTT is carried out, the blood sugar level of a diabetic will be in excess of 200 mg of glucose per dL (11.1 mmol/l) of plasma 2 hours after 75 g of glucose have been taken on an empty stomach. In a glucose tolerance test 75 g of glucose are administered orally to the patient being tested after a minimum of 8 hours, typically after 10-12 hours, of fasting and the blood sugar level is recorded immediately before taking the glucose and 1 and 2 hours after taking it. In a healthy subject, the blood sugar level before taking the glucose will be between 60 and 110 mg per dL of plasma, less than 200 mg per dL 1 hour after taking the glucose and less than 140 mg per dL after 2 hours. If after 2 hours the value is between 140 and 200 mg, this is regarded as abnormal glucose tolerance.

The term "late stage Type 2 diabetes mellitus" includes patients with a long-standing duration of diabetes, secondary drug failure, indication for insulin therapy and potentially progression to micro- and macrovascular complications e.g. diabetic nephropathy, or coronary heart disease (CHD).

The term "Type 1 diabetes" is defined as the condition in which a subject has, in the presence of autoimmunity towards the pancreatic beta-cell (i.e. detection of circulating islet cell autoantibodies ["type 1A diabetes mellitus"], i.e., at least one of: GAD65 [glutamic acid decarboxylase-65], ICA [islet-cell cytoplasm], IA-2 [intracytoplasmatic domain of the tyrosine phosphatase-like protein IA-2], ZnT8 [zinc-transporter-8] or anti-insulin; or other signs of autoimmunity without the presence of typical circulating autoantibodies [type 1B diabetes], i.e. as detected through pancreatic biopsy or imaging), a fasting (i.e., no caloric intake for 8 hours) blood glucose or serum glucose concentration greater than 125 mg/dL (6.94 mmol/L). Type 1 diabetes is also defined as the condition in which a subject has, in the presence of autoimmunity towards the pancreatic beta-cell, HbA1c equal to, or greater than 6.5%, a two hour plasma glucose equal to, or greater than 200 mg/dL (11.1 mmol/L) during an oral glucose tolerance test (OGTT) or a random glucose equal to, or greater than 200 mg/dL (11.1 mmol/L) in conjunction with classic symptoms of hyperglycaemia or hyperglycaemic crisis. In the absence of uneqicoval hyperglycaemia, as with most diagnostic tests, a test result diagnostic of diabetes should be repeated to rule out laboratory error. The measurement of blood glucose values is a standard procedure in routine medical analysis. The assessment of HbA1c should be performed using a method certified by the National Glycohemoglobin Standardization Program (NGSP) and standardized or traceable to the Diabetes Control and Complications Trial (DCCT) reference assay. If an OGTT is carried out, the blood sugar level of a diabetic will be in excess of 200 mg of glucose per dL (11.1 mmol/l) of plasma 2 hours after 75 g of glucose have been taken on an empty stomach, in the presence of autoimmunity towards the pancreatic beta cell. In a glucose tolerance test 75 g of glucose are administered orally to the patient being tested after a minimum of 8 hours, typically, 10-12 hours, of fasting and the blood sugar level is recorded immediately before taking the glucose and 1 and 2 hours after taking it. Typically a genetic predisposition is present (e.g. HLA, INS VNTR and PTPN22), but this is not always the case.

The term "MODY" ("maturity onset diabetes of the youth") describes a monogenic form for diabetes that, according to gene affects, is split into MODY variants, e.g., MODY 1,2.3.4 etc.

The term "LADA" ("latent autoimmune diabetes of adults") refers to patients that has a clinical diagnosis of Type 2 Diabetes Mellitus, but who is being detected to have autoimmunity towards the pancreatic beta cell.

The term "HbA1c" refers to the product of a non-enzymatic glycation of the haemoglobin B chain. Its determination is well known to one skilled in the art. In monitoring the treatment of diabetes mellitus the HbA1c value is of exceptional importance. As its production depends essentially on the blood sugar level and the life of the erythrocytes, the HbA1c in the sense of a "blood sugar memory" reflects the average blood sugar levels of the preceding 4-6 weeks. Diabetic patients whose HbA1c value is consistently well adjusted by intensive diabetes treatment (i.e. <6.5% of the total haemoglobin in the sample), are significantly better protected against diabetic microangiopathy. For example, metformin on its own achieves an average improvement in the HbA1c value in the diabetic of the order of 1.0-1.5%. This reduction of the HbA1C value is not sufficient in all diabetics to achieve the desired target range of <6.5% and preferably <6% HbA1c.

The term "insufficient glycemic control" or "inadequate glycemic control" in the scope of the present invention means a condition wherein patients show HbA1c values above 6.5%, in particular above 7.0%, even more preferably above 7.5%, especially above 8%.

The "metabolic syndrome", also called "syndrome X" (when used in the context of a metabolic disorder), also called the "dysmetabolic syndrome" is a syndrome complex with the cardinal feature being insulin resistance (Laaksonen D E, et al. *Am J Epidemiol* 2002; 156:1070-7). According to the ATP III/NCEP guidelines (Executive Summary of the Third Report of the National Cholesterol Education Program (NCEP) Expert Panel on Detection, Evaluation, and Treatment of High Blood Cholesterol in Adults (Adult Treatment Panel III) *JAMA: Journal of the American Medical Association* (2001) 285:2486-2497), diagnosis of the metabolic syndrome is made when three or more of the following risk factors are present:

1. Abdominal obesity, defined as waist circumference greater than about 40 inches or 102 cm in men, and greater than about 35 inches or 94 cm in women;
2. Triglycerides equal to or greater than about 150 mg/dL;
3. HDL-cholesterol less than about 40 mg/dL in men and less than about 50 in women;
4. Blood pressure equal to or greater than about 130/85 mm Hg (SBP equal to or greater than about 130 or DBP equal to or greater than about 85);
5. Fasting blood glucose equal to or greater than about 100 mg/dL.

According to a commonly used definition, hypertension is diagnosed if the systolic blood pressure (SBP) exceeds a value of 140 mm Hg and diastolic blood pressure (DBP) exceeds a value of 90 mm Hg. If a patient is suffering from manifest diabetes it is currently recommended that the systolic blood pressure be reduced to a level below 130 mm Hg and the diastolic blood pressure be lowered to below 80 mm Hg.

The definitions of NODAT (new onset diabetes after transplantation) and PTMS (post-transplant metabolic syndrome) follow closely that of the American Diabetes Association diagnostic criteria for type 2 diabetes, and that of the International Diabetes Federation (IDF) and the American Heart Association/National Heart, Lung, and Blood Institute, for the metabolic syndrome. NODAT and/or PTMS are associated with an increased risk of micro- and macrovascular disease and events, graft rejection, infection, and death. A number of predictors have been identified as potential risk factors related to NODAT and/or PTMS including a higher age at transplant, male gender, the pre-transplant body mass index, pre-transplant diabetes, and immunosuppression.

The term "gestational diabetes" (diabetes of pregnancy) denotes a form of the diabetes which develops during pregnancy and usually ceases again immediately after the birth. Gestational diabetes is diagnosed by a screening test which often is carried out between the 24th and 28th weeks of pregnancy, but could be conducted at any time during pregnancy, in particular if previous gestational diabetes has been diagnosed. It is usually a simple test in which the blood sugar level is measured e.g., one hour after the administration of 50 g of glucose solution. If this 1 h level is above 140 mg/dl, gestational diabetes is suspected. Final confirmation may be obtained by a standard glucose tolerance test, for example with 75 g of glucose; which also serve as a diagnostic test in the absence of the 50 g challenge.

As used herein, unless otherwise noted, the term "obesity related disorder" shall mean any disease, disorder or condition which is characterized by excess body weight or any disease, disorder or condition which is exacerbated, intensified or whose progression is accelerated as a result of excess weight. Also included is any disease, disorder or condition where at least on symptom or manifestation of said disease, disorder or condition is exacerbated, intensified or whose progression is accelerated as a result of excess weight. Suitably examples of obesity related disorders include, but are not limited to (a) overweight or obesity;

(b) metabolic disorders such as pre-diabetes, impaired oral glucose tolerance, impaired fasting blood glucose, insulin resistance, Type 1 diabetes mellitus, Type 2 diabetes mellitus, maturity onset diabetes of the youth (MODY), latent autoimmune diabetes of adults (LADA), NODAT, gestational diabetes, hyperglycemia, post prandial hyperglycemia, hyperinsulinemia, insufficient glycemic control (or inadequate glycemic control) and Syndrom X (also known as Metabolic Syndrome), and the like;

(c) renal or fatty liver disorders (such as alcoholic simple fatty liver, alcoholic steatohepatitis (ASH), alcoholic hepatic fibrosis, alcoholic cirrhosis, nonalcoholic fatty liver disease (NAFLD), nonalcoholic simple fatty liver, nonalcoholic steatohapatitis (NASH), nonalcoholic hepatic fibrosis, and nonalcoholic cirrhosis, hyperfiltrative diabetic nephropathy, renal hyperfiltration, glomerular hyperfiltration, renal allograft hyperfiltration, compensatory hyperfiltration, hyperfiltrative chronic kidney disease, hyperfiltrative acute renal failure, microalbuminuria (elevated urine albumin levels), macroalbuminuria, elevated urine albumin levels, elevated albumin/creatinine ratio (ACR), chronic kidney disease (CKD), acute renal failure (ARF), and the like;

(d) MACE or cardiovascular events (such as myocardial infarction, unstable angina, cardiovascular death, revascularization, fatal/nonfatal cerebrovascular accident, peripheral arteriopathy, aortic event, hospitalization due to congestive heart failure, and the like);

and (e) sleep disorders (such as sleep apnea, and the like).

The term "subject" as used herein, refers to an animal, preferably a mammal, most preferably a human, who has been the object of treatment, observation or experiment.

In certain embodiments of the present invention, the subject is overweight or obese. In additional embodiments of the present invention, the subject is overweight or obese and has been diagnosed with or exhibits at least one symptom of an obesity related disorder. In additional embodiments of the present invention, the subject is has a measured or determined BMI is greater than or equal to about 25 kg/m$^2$, preferably greater than or equal to about 30 kg/m$^2$.

In certain embodiments of the present invention, the subject is diabetic. In certain embodiments of the present invention, the subject is pre-diabetic. In certain embodiments of the present invention, the subject is non-diabetic.

As used herein, unless otherwise noted, the terms "treating", "treatment" and the like, shall include the management and care of a subject or patient (preferably a mammal, more preferably a human) for the purpose of combating a disease, condition, or disorder. The terms "treating" and "treatment" include the administration of the compound(s) or pharmaceutical composition(s) as described herein to (a) alleviate one or more symptoms or complications of the disease, condition or disorder; (b) prevent the onset of one or more symptoms or complications of the disease, condition or disorder; and/or (c) eliminate one or more symptoms or complications of the disease, condition, or disorder.

As used herein, unless otherwise noted, the terms "delaying the progression of" and "slowing the progression of" shall include (a) delaying or slowing the development of one or more symptoms or complications of the disease, condition or disorder; (b) delaying or slowing the development of one or more new/additional symptoms or complications of the disease, condition or disorder; and/or (c) delaying or slowing the progression of the disease, condition or disorder to a later stage or more serious form of said disease, condition or disorder.

As used herein, unless otherwise noted, the terms "preventing" and "prevention" shall include (a) reducing the frequency of one or more symptoms; (b) reducing the severity of one or more symptoms; (c) delaying, slowing or avoiding the development of one or more additional symptoms; and/or (d) delaying, slowing or avoiding the development of the disorder, condition or disease to a later stage or more serious form.

One skilled in the art will recognize that wherein the present invention is directed to methods of prevention, a subject in need of thereof (i.e. a subject in need of prevention) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical profession to be at risk of developing said disorder, disease or condition. For example, the subject may be deemed at risk of developing a disorder, disease or condition (and therefore in need of prevention or preventive treatment) as a consequence of the subject's medical history, including, but not limited to, family history, pre-disposition, co-existing (co-morbid) disorders or conditions, genetic testing, and the like.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

Wherein the present invention is directed to co-therapy or combination therapy, comprising administration of (a) canagliflozin and (b) phentermine "therapeutically effective amount" shall mean that amount of the combination of agents taken together so that the combined effect elicits the desired biological or medicinal response. For example, the therapeutically effective amount of co-therapy comprising administration of (a) canagliflozin and (b) phentermine would be the amount of (a) canagliflozin and the amount of (b) phentermine that when taken together or sequentially have a combined effect that is therapeutically effective. Further, it will be recognized by one skilled in the art that in the case of co-therapy or combination therapy with a therapeutically effective amount, as in the example above, the amount of (a) canagliflozin) and/or the amount of (b) phentermine individually may or may not be therapeutically effective.

As used herein, the terms "co-therapy" and "combination therapy" shall mean treatment of a subject in need thereof by administering (a) canagliflozin and (b) phentermine, wherein the (a) canagliflozin and (b) phentermine are administered by any suitable means, simultaneously, sequentially, separately or in a single pharmaceutical formulation (as long as the canagliflozin and phentermine are present in the subject, to some extent, at the same time). Where the (a) canagliflozin and (b) phentermine are administered in separate dosage forms, the number of dosages administered per day for each compound may be the same or different. The (a) canagliflozin and (b) phentermine may be administered via the same or different routes of administration. Examples of suitable methods of administration include, but are not limited to, oral, intravenous (iv), intramuscular (im), subcutaneous (sc), transdermal, and rectal. The (a) canagliflozin and (b) phentermine may also be administered directly to the nervous system including, but not limited to, intracerebral, intraventricular, intracerebroventricular, intrathecal, intracisternal, intraspinal and/or peri-spinal routes of administration by delivery via intracranial or intravertebral needles and/or catheters with or without pump devices. The (a) canagliflozin and (b) phentermine may be administered according to simultaneous or alternating regimens, at the same or different times during the course of the therapy, concurrently in divided or single forms.

The present invention is directed to combination therapy or co-therapy as described herein. Combination therapy or co-therapy is advantageous because in certain instances, the co-administration of active ingredients achieves a therapeutic effect that is greater than the therapeutic effect achieved by administration of only a single therapeutic agent.

In certain embodiments, the co-administration (combination therapy or co-therapy) of two or more therapeutic agents achieves a therapeutic effect that is greater than the therapeutic effect achieved by administration of only a single therapeutic agent. In this regard, the therapeutic effect of one therapeutic agent is augmented by the co-administration of another therapeutic agent. In certain embodiments, the co-administration of two or more therapeutic agents achieves a therapeutic effect that is equal to about the sum of the therapeutic effects achieved by administration of each single therapeutic agent. In these embodiments, the combination therapies are said to be "additive." In certain embodiments, the co-administration of two or more therapeutic agents achieves a synergistic effect, i.e., a therapeutic effect that is greater than the sum of the therapeutic effects of the individual components of the combination.

In certain embodiments, the therapeutic agents are administered in a single dosage form, wherein each individual therapeutic agent is isolated from the other therapeutic agent(s). Formulating the dosage forms in such a way assists in maintaining the structural integrity of potentially reactive therapeutic agents until they are administered. A formulation of this type may be useful during production and for long term storage of the dosage form. In certain embodiments, the therapeutic agents may comprise segregated regions or distinct caplets or the like housed within a capsule. In certain embodiments, the therapeutic agents are provided in isolated layers comprised by a tablet.

Alternatively, the therapeutic agents may be administered as separate compositions, e.g., as separate tablets or solutions. One or more active agent may be administered at the same time as the other active agent(s) or the active agents may be administered intermittently. The length of time between administrations of the therapeutic agents may be adjusted to achieve the desired therapeutic effect. In certain instances, one or more therapeutic agent(s) may be administered only a few minutes (e.g., about 1, 2, 5, 10, 30, or 60 min) after administration of the other therapeutic agent(s). Alternatively, one or more therapeutic agent(s) may be administered several hours (e.g., about 2, 4, 6, 10, 12, 24, or 36 hr) after administration of the other therapeutic agent(s). In certain embodiments, it may be advantageous to administer more than one dosage of one or more therapeutic agent(s) between administrations of the remaining therapeutic agent (s). For example, one therapeutic agent may be administered at 2 hours and then again at 10 hours following administration of the other therapeutic agent(s). Importantly, it is required that the therapeutic effects of each active ingredient overlap for at least a portion of the duration of each therapeutic agent so that the overall therapeutic effect of the combination therapy is attributable in part to the combined or synergistic effects of the combination therapy.

Since two or more different active agents are being used together in a combination therapy, the potency of each agent and the interactive effects achieved using them together must be considered. Importantly, the determination of dosage ranges and optimal dosages for a particular mammal is also well within the ability of one of ordinary skill in the art having the benefit of the instant disclosure.

The term "synergistic" refers to a combination which is more effective than the additive effects of any two or more single agents. A synergistic effect permits the effective treatment of a disease, disorder or condition using lower amounts (doses) of individual therapy. The lower doses result in lower toxicity without reduced efficacy. In addition, a synergistic effect can result in improved efficacy. Finally, synergy may result in an improved avoidance or reduction of disease as compared to any single therapy.

Combination therapy can allow for the product of lower doses of the first therapeutic or the second therapeutic agent (referred to as "apparent one-way synergy" herein), or lower doses of both therapeutic agents (referred to as "two way synergy" herein) than would normally be required when either drug is used alone. In certain embodiments, the synergism exhibited between one or more therapeutic agent(s) and the remaining therapeutic agent(s) is such that the dosage of one of the therapeutic agents would be sub-therapeutic if administered without the dosage of the other therapeutic agents.

The terms "augmentation" or "augment" refer to combinations where one of the compounds increases or enhances therapeutic effects of another compound or compounds administered to a patient. In some instances, augmentation can result in improving the efficacy, tolerability, or safety, or any combination thereof, of a particular therapy.

In certain embodiments, the present invention relates to a pharmaceutical composition comprising a therapeutically effective dose of one or more therapeutic agent(s) together with a dose of another therapeutic agent effective to augment the therapeutic effect of the one or more therapeutic agent(s). In other embodiments, the present invention relates to methods of augmenting the therapeutic effect in a patient of one or more therapeutic agent(s) by administering another therapeutic agent to the patient.

In certain embodiments, the invention is directed in part to synergistic combinations of one or more therapeutic agent(s) in an amount sufficient to render a therapeutic effect together with the remaining therapeutic agent(s). For example, in certain embodiments a therapeutic effect is attained which is at least about 2 (or at least about 4, 6, 8, or 10) times greater than that obtained with the dose of the one or more therapeutic agent(s) alone. In certain embodiments, the synergistic combination provides a therapeutic effect which is up to about 20, 30 or 40 times greater than that obtained with the dose of the one or more therapeutic agent(s) alone. In such embodiments, the synergistic combinations display what is referred to herein as an "apparent one-way synergy", meaning that the dose of the remaining therapeutic agent(s) synergistically potentiates the effect of the one or more therapeutic agent(s), but the dose of the one or more therapeutic agent(s) does not appear to significantly potentiate the effect of the remaining therapeutic agent(s).

In certain embodiments, the combination of active agents exhibits two-way synergism, meaning that the second therapeutic agent potentiates the effect of the first therapeutic agent, and the first therapeutic agent potentiates the effect of the second therapeutic agent. Thus, other embodiments of the invention relate to combinations of a second therapeutic agent and a first therapeutic agent where the dose of each drug is reduced due to the synergism between the drugs, and the therapeutic effect derived from the combination of drugs in reduced doses is enhanced. The two-way synergism is not always readily apparent in actual dosages due to the potency ratio of the first therapeutic agent to the second therapeutic agent. For instance, two-way synergism can be difficult to detect when one therapeutic agent displays much greater therapeutic potency relative to the other therapeutic agent.

The synergistic effects of combination therapy may be evaluated by biological activity assays. For example, the therapeutic agents are mixed at molar ratios designed to give approximately equipotent therapeutic effects based on the $EC_{90}$ or $EC_{50}$ values. Then, three different molar ratios are used for each combination to allow for variability in the estimates of relative potency. These molar ratios are maintained throughout the dilution series. The corresponding monotherapies are also evaluated in parallel to the combination treatments using the standard primary assay format. A comparison of the therapeutic effect of the combination treatment to the therapeutic effect of the monotherapy gives a measure of the synergistic effect. Further details on the design of combination analyses can be found in B E Korba (1996) Antiviral Res. 29:49. Analysis of synergism, additivity, or antagonism can be determined by analysis of the aforementioned data using the CalcuSyn™ program (Biosoft, Inc.). This program evaluates drug interactions by use of the widely accepted method of Chou and Talalay combined with a statistically evaluation using the Monte Carlo statistical package. The data are displayed in several different formats including median-effect and dose-effects plots, isobolograms, and combination index [CI] plots with standard deviations. For the latter analysis, a CI greater than 1.0 indicates antagonism and a CI less than 1.0 indicates synergism.

Compositions of the invention present the opportunity for obtaining relief from moderate to severe cases of disease. Due to the synergistic or additive or augmented effects provided by the inventive combination of the first and second therapeutic agent, it may be possible to use reduced dosages of each of therapeutic agent. By using lesser amounts of drugs, the side effects associated with each may be reduced in number and degree. Moreover, the inventive combinations avoid side effects to which some patients are particularly sensitive. The present invention provides pharmaceutically acceptable compositions which comprise a therapeutically effective amount of two or more of the compounds described herein, formulated together with one or more pharmaceutically acceptable carriers (additives) and/or diluents. As described in detail herein, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

For use in medicine, the salts of the compounds of this invention refer to non-toxic "pharmaceutically acceptable salts". Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases which may be used in the preparation of pharmaceutically acceptable salts include the following: acids including acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydrocy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitric acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value. Further, to provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein.

Pharmaceutical Compositions

As used herein, the term "composition" is intended to encompass a product comprising the specified ingredients in the specified amounts, as well as any product which results, directly or indirectly, from combinations of the specified ingredients in the specified amounts.

The present invention further comprises pharmaceutical compositions containing (a) canagliflozin, and (b) phentermine and a pharmaceutically acceptable carrier. Pharmaceutical compositions containing (a) canagliflozin and (b) phentermine as the active ingredients can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, (a) canagliflozin and (b) phentermine as the active ingredients are intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.1 mg to about 1000 mg, or any amount or range therein, and may be given at a dosage of from about 0.01-200.0 mg/kg/day, preferably from about 0.05 to 100 mg/kg/day, more preferably from about 0.05-50 mg/kg/day, more preferably from about 0.05-25.0 mg/kg/day, more preferably from about 0.05-10.0 mg/kg/day, most preferably from about 0.5 to about 7.5 mg/kg/day, or any range therein. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid pre-formulation composition containing a homogeneous mixture of a compound of the present invention, or a pharmaceutically acceptable salt thereof. When referring to these pre-formulation compositions as homogeneous, it is meant that the active ingredient is dispersed evenly throughout the composition so that the composition may be readily subdivided into equally effective dosage forms such as tablets, pills and capsules. This solid pre-formulation composition is then subdivided into unit dosage forms of the type described above containing from 0.1 to about 1000 mg, or any amount or range therein, of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

To prepare certain pharmaceutical compositions of the present invention, canagliflozin, as the active ingredient, and phentermine, as the active ingredient may each be intimately admixed with a pharmaceutical carrier according to conventional pharmaceutical compounding techniques, which carrier may take a wide variety of forms depending of the form of preparation desired for administration (e.g. oral or parenteral) and thereafter be separately combined together. To prepare further pharmaceutical compositions of the present invention, canagliflozin and phentermine, as the active ingredients, may be intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain, the disclosure of which is hereby incorporated by reference.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc., the disclosures of which are hereby incorporated by reference.

In addition to pharmaceutical solutions for the treatment of obesity, a variety of medical devices have been developed for use in the treatment of obesity, and are being introduced into clinical practice. While many of these devices are still in clinical trials, researchers remain optimistic regarding their prospects as components of low-severity, high-efficacy treatments for obesity. Moreover, the importance of these devices is magnified by the fact that many severely obese patients are not ideal candidates for surgical intervention. Therefore, such devices promise to provide new treatment options for patients suffering from obesity and other metabolic conditions, and in some cases may offer valuable alternatives to more invasive surgical approaches.

Endoluminal sleeves are one example of a device developed for the treatment of obesity. The sleeve creates a physical barrier between ingested food and the intestinal wall, thereby changing the metabolic pathway by controlling how food moves through the digestive system. This mechanical bypass of the small intestine mimics the effects on a patient's metabolism of gastric bypass surgery, often resulting in profound weight loss and remission of type 2 diabetes. The device can be implanted and removed endoscopically (via the mouth), without the need for surgical intervention.

Intragastric balloons are a second example. An intragastric balloon is designed to occupy volume within the stomach such that a smaller volume of food results in a feeling of satiety. Intragastric balloons currently on the market are not fixed in the stomach and, consequently, can lead to complications such as obstruction and mucosal erosion. To avoid these complications, the balloons are removed after a maximum of six months. One study found that the average excess weight loss was about 48.3% after one year. However, the patients reported occurrences of nausea and vomiting; and a smaller number of patients suffered from epigastric pain. Furthermore, balloon impaction occurred in about 0.6% of patients. A balloon which is fixed to the wall of the stomach could potentially improve the overall safety and efficacy of this approach, and allow longer-term implantation.

Devices have also been developed that reduce or reallocate the volume of a patient's gastrointestinal lumen. An example of such a device comprises an anchor that, once deployed, reduces a cross-sectional area within the GI track of a patient. A number of related devices in this class, such as staples, blind staples, bands, clips, tags, adhesives, and screws, have been used to reduce or reallocate the volume of a patient's stomach, specifically.

Another approach involves the use of electrical current to stimulate the stomach or certain nerves of the digestive tract. Medtronic (Minneapolis) has developed a battery-powered, stopwatch-size gastric pacemaker (similar to a cardiac pacemaker) that causes the stomach to contract, sending signals of satiety to the appetite center in the brain. The gastric pacemaker is implanted under the skin of the abdomen with electric wires placed on the wall of the stomach. Additionally, the electricity will modify eating behavior by regulating appetite signals. Moreover, the gastric pacemaker may also work to boost metabolism, which can lead to further weight loss.

An implant that uses electrical charges to inhibit the main nerve (vagus nerve) leading to the stomach has also been developed. In this case, the electrical charge may slow down digestion; for example, due to the stimulation the stomach would not register that presence of food and, therefore, would not initiate the digestive process. By down-regulating the activity of the vagus nerve, the technology simultaneously controls multiple major biological functions related to obesity, including food intake, hunger perception and digestion. Furthermore, the modulation is reversible, and the therapy can be adjusted and programmed to meet an individual patient's treatment needs.

Deep-brain-stimulation technology is also being developed as a possible treatment for obesity, which uses tiny electrodes implanted in specific areas of the brain to affect behavior, movement and other functions. Brain stimulation technology is currently approved in the United States to treat movement disorders, such as Parkinson's disease, and is being studied to treat obsessive compulsive disorder and severe depression.

Also being examined are devices that deliver an electrical charge to the same parts of the nervous system that are activated by exercise, which is known to be associated with increased metabolism. Such devices may be able to help people lose weight by boosting their metabolism.

The methods of the present invention may also be carried out using a pharmaceutical composition comprising (a) canagliflozin and (b) phentermine as defined herein and a pharmaceutically acceptable carrier. The pharmaceutical composition may contain between about 0.1 mg and 1000 mg, or any amount or range therein, preferably about 2.5 to 500 mg, of each of the canagliflozin and phentermine, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, the (a) canagliflozin and (b) phentermine co-therapy of the present invention may be administered in a single daily dose, or the total daily dosage may be administered in divided doses of two, three or four times daily. Furthermore, the (a) canagliflozin and (b) phentermine of the co-therapy of the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the (a) canagliflozin and (b) phentermine can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The co-therapy of the present invention, and the (a) canagliflozin and (b) phentermine which comprise said co-therapy may be administered in any of the foregoing compositions and according to dosage regimens established in the art whenever treatment of depression is required.

The daily dosage of each of canagliflozin, phentermine and/or the co-therapy comprising canagliflozin and phentermine may be varied over a wide range from 0.01 to 150 mg/kg per adult human per day. For oral administration, each of canagliflozin, phentermine and/or the co-therapy comprising canagliflozin and phentermine may be preferably provided in the form of tablets containing, 0.01, 0.05, 0.1, 0.5, 1.0, 2.5, 3.75, 5.0, 7.5, 10.0, 15.0, 25.0, 30.0, 37.5, 50.0, 100, 150, 200, 250, 300, 500 and 1000 milligrams of the active ingredient(s) for the symptomatic adjustment of the dosage to the patient to be treated. An effective amount of the active ingredient(s) is ordinarily supplied at a dosage level of from about 0.01 mg/kg to about 1500 mg/kg of body weight per day. Preferably, the range is from about 0.05 to about 100.0 mg/kg of body weight per day, more preferably, from about 0.05 mg/kg to about 50 mg/kg, more preferably, from about 0.05 to about 25.0 mg/kg of body weight per day. The active ingredient(s) may be administered on a regimen of 1 to 4 times per day, concurrently, sequentially, separately or in a single dosage form.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

The following Examples are set forth to aid in the understanding of the invention, and are not intended and should not be construed to limit in any way the invention set forth in the claims which follow thereafter.

EXAMPLE 1

Clinical Trial

Co-Therapy with 300 mg Canagliflozin and 15 mg Phentermine

The safety and efficacy of combination treatment with 300 mg canagliflozin and 15 mg phentermine was investigated in a 26 week, randomized, double-blind, placebo-controlled, parallel group, multi-center study. (Complete study protocol filed and available as STUDY 28431754-OBE2002 on www.clinicaltrials.gov).

Trial Design:

The study began with a 4-week single blind placebo run-in period. After completing the run-in period 335 overweight or obese non-diabetic adult subjects who had a BMI ≥30 kg/m$^2$ and <50 kg/m$^2$ at screening; or BMI ≥27 kg/m$^2$ and <50 kg/m$^2$ at screening in the presence of a comorbidity/comorbidities of hypertension and/or dyslipidemia were randomly assigned in a 1:1:1:1 ratio to treatment with (A) canagliflozin 300 mg and phentermine 15 mg, (B) canagliflozin 300 mg, (C) phentermine 15 mg, or (D) placebo with the stratification factor: run-in weight loss of ≤2 kg or >2 kg. All subjects were provided with diet and exercise counseling for weight loss (standardized non-pharmacological therapy) and were instructed to follow the diet and exercise program throughout the study.

The modified intent-to-treat (mITT) analysis set included all randomized subjects who had received at least one dose of study drug. The primary efficacy endpoint was percent change from baseline in body weight at Week 26. The secondary efficacy endpoints included (1) proportion of subjects with weight loss ≥5% at Week 26, (2) absolute change from baseline in SBP (static blood pressure) at Week 26, and (3) absolute change from baseline in body weight at Week 26. The inclusion of canagliflozin 300 mg and phentermine 15 mg as separate treatment groups allowed for a descriptive estimate of relative contribution of the individual components to the observed weight loss in the co-therapy canagliflozin 300 mg/phentermine 15 mg group and provided efficacy and safety data on canagliflozin 300 mg in the non-diabetic, overweight/obese population. Safety analyses included treatment-emergent adverse events (referred to as adverse events in this document), laboratory tests (including chemistry and hematology), and vital signs (blood pressure and pulse rate).

There were 335 subjects randomized and 334 subjects dosed; 334 subjects comprised the mITT analysis set of whom 231 (69%) completed the study. One subject was inadvertently randomized after not meeting eligibility criteria and was not dosed. The proportion of subjects who discontinued was lower in the co-administration of canagliflozin 300 mg and phentermine 15 group compared to the other treatment groups. Overall, lost to follow-up and adverse event were the most frequent reasons for discontinuation (12.9% and 7.5%, respectively). No subjects discontinued due to a serious adverse event (SAE).

The majority of subjects were female (81.7%), white (78.4%), mean age of 45.7 years, mean baseline $HbA_{1c}$ of 5.6%, mean BMI of 37.3 kg/m$^2$, mean baseline weight of 102.9 kg, and mean eGFR of 95.8 mL/min/1.73 m$^2$. The minority of subjects (27.2%) lost more than 2 kg during the 4-week run-in period. Overall, baseline characteristics were generally similar across treatment groups.

Results:

Table 1 below, summarizes the effect of co-therapy of canagliflozin 300 mg/phentermine 15 mg versus placebo on body weight and systolic blood pressure (SBP).

TABLE 1

Results: Combination Treatment (canagliflozin 300 mg/phentermine 15 mg) vs Placebo (Week 26)

| Endpoint | Difference[b] | (95% CI)[b] | p-value[a] |
|---|---|---|---|
| Body Weight, % change from baseline | −6.9 | (−8.6; −5.2) | <0.001 |
| Proportions of subjects with weight loss ≥ 5% | 49.1 | (32.2; 66.1) | <0.001 |
| Body Weight at Week 26 Absolute change from baseline | −6.7 | (−8.5; −4.9) | <0.001 |
| SBP at Week 26 Absolute change from baseline | −4.2 | (−7.7; −0.8) | 0.015 |

[a]Nominal p-value
[b]Difference in proportions for achieving weight loss ≥ 5% endpoint; difference of LS Means for all other endpoints
NOTE:
For percent change from baseline in weight, absolute change from baseline in weight, and change from baseline in SBP, CIs and p-values are based on a mixed model for repeated measures including the fixed effects of treatment, weight loss during run-in, visit, treatment-by-visit interaction, baseline value and baseline-by-visit interaction, and subject as a random effect. For achieving at least 5% weight loss, CI is based on Normal approximation to binomial distribution with continuity correction; p-value is based on the generalized linear mixed model for repeated measures including the fixed effects of treatment, weight loss during run-in, visit, treatment-by-visit interaction, treatment-by-subgroup interaction, baseline value and baseline-by-visit interaction, and subject as a random effect.

Treatment with co-therapy of canagliflozin 300 mg/phentermine 15 mg achieved statistical significance versus placebo with respect to the percent change from baseline in weight at Week 26 (−7.5% vs 0.6%, respectively, p<0.001). The primary weight loss endpoint at week 26, as measured, is shown in a graph of observed weight loss (as the mean placebo-subtracted weight loss at each time point) in FIG. 1, open symbols. More specifically, co-administration of 300 mg canagliflozin and 15 mg phentermine was associated with a statistically significant placebo-subtracted weight loss of −6.9%. Additionally, at the endpoint of Week 26, no plateau in weight loss was observed, indicating that weight loss would be expected to continue beyond Week 26. The proportion of subjects who achieved at least 5% weight reduction was 66.7% in the co-administration arm, compared to 17.5% for placebo. The proportion of subjects with a weight loss of at least 10% was 34.9% in the co-administration group, vs. 8.8% with placebo. (Thus, at Week 26, the study met both benchmarks considered effective for weight management by the FDA: "after 1 year of treatment either of the following occurs: the difference in mean weight loss between the active-product and placebo-treated groups is at least 5 percent and the difference is statistically significant, or the proportion of subjects who lose greater than or equal to 5 percent of baseline body weight in the active-product group is at least 35 percent, is approximately double the proportion in the placebo-treated group, and the difference between groups is statistically significant.) Based on the Week 26 weight loss over time data measured in the study, extrapolation (exponential fit) to estimate weight loss at 1 year, indicated a potential placebo-subtracted weight loss of −8.8% for the co-administration group, as shown by the solid line in FIG. 1.

It is estimated that with respect to the weight loss observed at Week 26, phentermine alone contributes 50%, canagliflozin alone contributes 18% and the interaction contributes 32%.

Table 2 below provides percent change from baseline for body weight at Week 26 for each of the treatment groups of the study: (A) combination treatment with canagliflozin 300 mg and phentermine 15 mg, (B) canagliflozin 300 mg, (C) phentermine 15 mg and (D) placebo.

TABLE 2

% Change from Baseline, Body Weight at Week 26

|  | Placebo (N = 82) | Phen 15 mg (N = 85) | Cana 300 mg (N = 84) | Cana 300 mg/ Phen 15 mg (N = 83) |
|---|---|---|---|---|
| Weight (kg) Value at Baseline | | | | |
| N | 76 | 76 | 78 | 77 |
| Mean (SD) | 104.00 (18.344) | 102.43 (18.606) | 103.33 (19.626) | 100.06 (18.125) |
| % Change from Baseline at Week 26 | | | | |
| LS Mean (SE) | −0.6 (0.6) | −4.1 (0.6) | −1.9 (0.6) | −7.5 (0.6) |
| Minus Placebo[a] | | | | |
| P-value | | <0.001 | 0.142 | <0.001 |
| Diff. of LS Means (SE) | | −3.5 (0.9) | −1.3 (0.9) | −6.9 (0.9) |
| 95% CI[a] | | (−5.3; −1.8) | (−3.1; 0.4) | (−8.6; −5.2) |

TABLE 2-continued

% Change from Baseline, Body Weight at Week 26

|  | Placebo (N = 82) | Phen 15 mg (N = 85) | Cana 300 mg (N = 84) | Cana 300 mg/ Phen 15 mg (N = 83) |
|---|---|---|---|---|
| Minus Phentermine 15 mg[a] | | | | |
| P-value | | | | <0.001 |
| Diff. of LS Means (SE) | | | | -3.4 (0.9) |
| 95% CI[a] | | | | (-5.1; -1.6) |
| Minus Canagliflozin 300 mg[a] | | | | |
| P-value | | | | <0.001 |
| Diff. of LS Means (SE) | | | | -5.6 (0.9) |
| 95% CI[a] | | | | (-7.3; -3.8) |

[a]Pairwise comparison: CIs and P values are based on a mixed model for repeated measures including the fixed effects of treatment, weight loss during run-in, visit, treatment-by-visit interaction, baseline value and baseline-by-visit interaction, and subject as a random effect.
Note:
The table includes only the subjects who had both baseline and post-baseline body weight measurements.

The change from baseline in absolute body weight at Week 26 was analyzed with an MMRM similar to the primary efficacy endpoint. The categorical secondary efficacy endpoint (proportion of subjects with weight loss ≥5% at Week 26) was analyzed with a generalized linear mixed model which is similar to the MMRM approach, though suitable for longitudinal binary data, with results as shown in Table 3, below.

TABLE 3

Absolute Body Weight Change from Baseline, Week 26

|  | Placebo (N = 82) | Phen 15 mg (N = 85) | Cana 300 mg (N = 84) | Cana 300 mg/ Phen 15 mg (N = 83) |
|---|---|---|---|---|
| Weight (kg) Value at Baseline | | | | |
| N | 76 | 76 | 78 | 77 |
| Mean (SD) | 104.00 (18.344) | 102.43 (18.606) | 103.33 (19.626) | 100.06 (18.125) |
| Change from Baseline at Week 26 | | | | |
| LS Mean (SE) | -0.6 (0.6) | -4.1 (0.6) | -1.9 (0.7) | -7.3 (0.6) |
| Minus Placebo[a] | | | | |
| P-value | | <0.001 | 0.153 | <0.001 |
| Diff. of LS Means (SE) | | -3.5 (0.9) | -1.3 (0.9) | -6.7 (0.9) |
| 95% CI (a) | | (-5.3; -1.7) | (-3.1; 0.5) | (-8.5; -4.9) |
| Minus Phen 15 mg[a] | | | | |
| P-value | | | | <0.001 |
| Diff. of LS Means (SE) | | | | -3.2 (0.9) |
| 95% CI (a) | | | | (-4.9; -1.4) |
| Minus Cana 300 mg[a] | | | | |
| P-value | | | | <0.001 |
| Diff. of LS Means (SE) | | | | -5.4 (0.9) |
| 95% CI (a) | | | | (-7.1; -3.6) |

[a]Pairwise comparison: CIs and P values are based on a mixed model for repeated measures including the fixed effects of treatment, weight loss during run-in, visit, treatment-by-visit interaction, baseline value and baseline-by-visit interaction, and subject as a random effect.
Note:
The table includes only the subjects who had both baseline and post-baseline body weight measurements.

In addition to the effect on weight loss, a significant placebo-subtracted reduction in systolic blood pressure of -4.2 mm Hg (baseline 125 mm Hg) was observed in the co-administration treatment group (the absolute change in SBP at Week 26 was -6.9 mmHg vs. -2.7 mmHg for the placebo controlled group, p=0.015). The reduction in diastolic blood pressure of -1.6 mm Hg (baseline 80 mm Hg) was not statistically significant. The change from baseline in systolic blood pressure at Week 26 was analyzed with an MMRM similar to the primary efficacy endpoint, with results as shown in Table 4, below.

TABLE 4

Change From Baseline, Systolic Blood Pressure, Week 26

| | Placebo (N = 82) | Phen 15 mg (N = 85) | Cana 300 mg (N = 84) | Cana 300 mg/ Phen 15 mg (N = 83) |
|---|---|---|---|---|
| Systolic blood pressure (mmHg), Value at Baseline | | | | |
| N | 75 | 76 | 78 | 77 |
| Mean (SD) | 124.22 (12.937) | 124.05 (11.491) | 124.81 (13.309) | 125.26 (13.068) |
| Change From Baseline | | | | |
| LS Mean (SE) | −2.7 (1.3) | −1.4 (1.2) | −3.1 (1.3) | −6.9 (1.2) |
| Minus Placebo[a] | | | | |
| P-value | | 0.456 | 0.827 | 0.015 |
| Diff. of LS Means (SE) | | 1.3 (1.8) | −0.4 (1.8) | −4.2 (1.7) |
| 95% CI (a) | | (−2.1; 4.8) | (−3.9; 3.1) | (−7.7; −0.8) |
| Minus Phen 15 mg[a] | | | | |
| P-value | | | | 0.001 |
| Diff. of LS Means (SE) | | | | −5.6 (1.7) |
| 95% CI (a) | | | | (−8.9; −2.2) |
| Minus Cana 300 mg[a] | | | | |
| P-value | | | | 0.028 |
| Diff. of LS Means (SE) | | | | −3.9 (1.7) |
| 95% CI (a) | | | | (−7.3; −0.4) |

[a]Pairwise comparison: CIs and P values are based on a mixed model for repeated measures including the fixed effects of treatment, weight loss during run-in, visit, treatment-by-visit interaction, baseline value and baseline-by-visit interaction, and subject as a random effect.
Note:
The table includes only the subjects who had both baseline and post-baseline systolic blood pressure measurements.

The treatment arms containing phentermine 15 mg also appeared to increase pulse at Week 26, consistent with the known effects of phentermine (LS Mean change from baseline (SE)=4.1 (1.0) bpm and 3.5 (0.9) bpm for phentermine 15 mg and canagliflozin 300 mg/phentermine 15 mg, respectively, compared to −0.7 (1.0) bpm in the placebo group, and 0.7 (1.0) in the canagliflozin 300 mg group). Table 5 shows the mean and mean change from baseline for systolic blood pressure, diastolic blood pressure and pulse rate at Week 26.

TABLE 5

Mean & Mean Change for Blood Pressure, Pulse Rate at Week 26

| | Placebo (N = 82) | Phen 15 mg (N = 85) | Cana 300 mg (N = 84) | Cana 300 mg/ Phen 15 mg (N = 83) |
|---|---|---|---|---|
| Systolic Blood Pressure (mmHg) | | | | |
| N | 57 | 60 | 56 | 63 |
| Mean baseline | 125.27 | 123.39 | 124.70 | 125.28 |
| Mean change (SD) | −3.09 (10.967) | −1.13 (10.007) | −3.31 (11.349) | −7.08 (10.128) |
| (95% CI) | (−6.003; −0.184) | (−3.718; 1.452) | (−6.349; −0.270) | (−9.635; −4.534) |
| Median change | −2.00 | −0.33 | −1.67 | −6.00 |
| (95% CI) | (−6.000; 0.333) | (−3.000; 2.000) | (−6.000; 0.000) | (−8.333; −3.667) |
| Diastolic Blood Pressure (mmHg) | | | | |
| N | 57 | 60 | 56 | 63 |
| Mean baseline | 80.15 | 78.54 | 79.26 | 79.35 |
| Mean change (SD) | −1.08 (7.692) | 0.55 (6.864) | −1.32 (6.779) | −2.32 (6.705) |
| (95% CI) | (−3.123; 0.959) | (−1.223; 2.323) | (−3.131; 0.500) | (−4.006; −0.629) |
| Median change | −0.33 | 0.67 | −1.17 | −0.67 |
| (95% CI) | (−4.000; 1.667) | (−1.667; 2.667) | (−3.333; 0.333) | (−3.333; 0.333) |
| Pulse Rate (BEATS/MIN) | | | | |
| N | 57 | 60 | 56 | 63 |
| Mean baseline | 72.96 | 70.11 | 69.37 | 73.42 |
| Mean change (SD) | −0.89 (7.059) | 5.02 (7.568) | 1.64 (6.786) | 3.23 (9.800) |
| (95% CI) | (−2.762; 0.984) | (3.067; 6.977) | (−0.175; 3.460) | (0.760; 5.696) |

TABLE 5-continued

Mean & Mean Change for Blood Pressure, Pulse Rate at Week 26

|  | Placebo (N = 82) | Phen 15 mg (N = 85) | Cana 300 mg (N = 84) | Cana 300 mg/ Phen 15 mg (N = 83) |
|---|---|---|---|---|
| Median change | −1.00 | 4.67 | 0.83 | 3.67 |
| (95% CI) | (−4.000; 1.333) | (1.667; 6.667) | (−1.000; 2.667) | (0.667; 5.333) |

Note:
For each measurement, only the subjects who had both baseline and post baseline measurements are included.

FORMULATION EXAMPLE 1

Prophetic Example

As a specific embodiment of an oral composition, 300 mg of canagliflozin and 15 mg of phentermine are formulated with sufficient finely divided lactose to provide a total amount of 580 to 590 mg to fill a size O hard gel capsule.

FORMULATION EXAMPLE 2

Prophetic Example

As a specific embodiment of an oral composition, 300 mg of canagliflozin and 15 mg of phentermine are formulated with lactose and microcrystalline cellulose to provide a tablet of total weight in the amount of about 600 mg to about 620 mg.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A method for chronic weight management comprising administering to a subject in need thereof a therapeutically effective amount of co-therapy comprising (a) canagliflozin and (b) phentermine;
   wherein the canagliflozin is administered in an amount of about 300 mg;
   wherein the phentermine is administered in an amount of about 15 mg; and
   wherein the subject in need thereof is a subject with an initial body mass index greater than or equal to about 30 kg/m2; or greater than or equal to about 27 kg/m2 and diagnosed with or exhibiting at least one weight-related co-morbid condition.

2. The method of claim 1, wherein the subject in need thereof is overweight or obese.

3. The method of claim 1, wherein the subject in need thereof is overweight or obese; and wherein the subject in need thereof has been diagnosed with or exhibits one or more symptoms of a disorder selected from the group consisting of pre-diabetes, impaired oral glucose tolerance, Type II diabetes mellitus, Metabolic Syndrome, cardiovascular risk, renal or fatty liver disorder and sleep apnea.

4. The method of claim 1, wherein the subject in need thereof has been diagnosed with or shows one or more symptoms of one or more of the following conditions: (a) diabetes mellitus, regardless of type; (b) chronic kidney disease (CKD); (c) acute renal failure (ARF); (d) renal transplant recipients; (e) renal transplant donors; (f) unilateral total or partial nephrectomized patients; or (g) nephrotic syndrome.

5. The method of claim 1, wherein the subject in need thereof is diabetic or pre-diabetic.

6. The method of claim 1, wherein the subject in need thereof is non-diabetic.

7. The method of claim 1, wherein the co-therapy is an adjunct to a reduced-calorie diet and increased physical activity.

8. The method of claim 1, wherein the canagliflozin is administered as a crystalline hemihydrate.

9. The method of claim 1, wherein the phentermine is phentermine hydrochloride.

10. A pharmaceutical composition comprising
    (a) canagliflozin in an amount of about 300 mg;
    (b) phentermine an amount of about 15 mg; and
    (c) a pharmaceutically acceptable carrier or excipient.

* * * * *